(12) United States Patent
Emerling et al.

US009493813B2

(10) Patent No.: US 9,493,813 B2
(45) Date of Patent: Nov. 15, 2016

(54) MODULATION OF PHOSPHATIDYLINOSITOL-5-PHOSPHATE-4-KINASE ACTIVITY

(75) Inventors: Brooke Emerling, Boston, MA (US); Atsuo Sasaki, Newton, MA (US); Lewis C. Cantley, Cambridge, MA (US); Jonathan Hurov, Cambridge, MA (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 0 days.

(21) Appl. No.: 13/985,462

(22) PCT Filed: Jan. 13, 2012

(86) PCT No.: PCT/US2012/021266
§ 371 (c)(1),
(2), (4) Date: Nov. 26, 2013

(87) PCT Pub. No.: WO2012/112245
PCT Pub. Date: Aug. 23, 2012

(65) Prior Publication Data
US 2014/0080893 A1    Mar. 20, 2014

Related U.S. Application Data

(60) Provisional application No. 61/442,622, filed on Feb. 14, 2011.

(51) Int. Cl.
*C12Q 1/68* (2006.01)
*C12Q 1/48* (2006.01)
*A61K 31/7105* (2006.01)
*C12N 15/11* (2006.01)

(52) U.S. Cl.
CPC .......... *C12Q 1/485* (2013.01); *A61K 31/7105* (2013.01); *G01N 2500/02* (2013.01); *G01N 2500/10* (2013.01)

(58) Field of Classification Search
CPC .............. C12Q 1/6886; C12Q 1/485; C12Q 2545/113; C12Q 2600/136; C12Q 1/00; C07K 14/4703; A61K 49/0008; C12N 15/113; C12N 15/1135; C12N 2310/14; C12N 2310/141; G01N 2500/02
See application file for complete search history.

(56) References Cited

U.S. PATENT DOCUMENTS

| | | | |
|---|---|---|---|
| 5,639,600 A | | 6/1997 | McGrath et al. |
| 6,071,726 A | * | 6/2000 | Diamandis et al. ......... 435/91.2 |
| 7,087,648 B1 | | 8/2006 | McGrath |
| 2006/0058255 A1 | | 3/2006 | Chen et al. |
| 2006/0089320 A1 | * | 4/2006 | Cantley et al. ................ 514/44 |
| 2007/0056049 A1 | * | 3/2007 | Ambs et al. ....................... 800/3 |
| 2010/0092456 A1 | * | 4/2010 | Bisset et al. ............... 424/130.1 |
| 2011/0245091 A1 | * | 10/2011 | Golovlev .......................... 506/7 |
| 2012/0076762 A1 | * | 3/2012 | Kawamura et al. ........ 424/93.21 |

OTHER PUBLICATIONS

Galiano et al., Overexpression of murine phosphatidylinositol 4-phosphate 5-kinase type I beta disrupts a phosphatidylinositol 4,5 bisphosphate regulated endosomal pathway, 2002, Journal of Cellular Biochemistry, vol. 85, pp. 131-145.*
Jones et al., Nuclear PtdIns5P as a transducer of stress signaling: An in vivo role for PIP4Kbeta, 2006, Molecular Cell, vol. 23, pp. 685-695.*
Chang et al., Involvement of PI3K/Akt pathway in cell cycle progression, apoptosis, and neoplastic transformation: a target for cancer chemotherapy, 2003, Leukemia, vol. 17, pp. 590-603.*
Baglioni et al., "Mechanisms of antiviral action of interferon," Interferon. 5:23-42 (1983).
Brady et al., "p53 at a glance," J Cell Sci. 123(Pt 15):2527-32 (2010).
Cantley, "The phosphoinositide 3-kinase pathway," Science. 296(5573):1655-7 (2002).
Carricaburu et al., "The phosphatidylinositol (PI)-5-phosphate 4-kinase type II enzyme controls insulin signaling by regulating PI-3,4,5-trisphosphate degradation," Proc Natl Acad Sci U S A. 100(17):9867-72 (2003).
Clarke et al., "Interactions between the double-stranded RNA binding motif and RNA: definition of the binding site for the interferon-induced protein kinase DAI (PKR) on adenovirus VA RNA," RNA. 1(1):7-20 (1995).
Demian et al., "High-throughput, cell-free, liposome-based approach for assessing in vitro activity of lipid kinases," J Biomol Screen. 14(7):838-44 (2009).
Elbashir et al., "Functional anatomy of siRNAs for mediating efficient RNAi in *Drosophila* melanogaster embryo lysate," EMBO J. 20(23):6877-88 (2001).
Gil et al., "Induction of apoptosis by the dsRNA-dependent protein kinase (PKR): mechanism of action," Apoptosis. 5(2):107-14 (2000).
Goh et al., "The role of mutant p53 in human cancer," J Pathol. 223(2):116-26 (2011).
Gozani et al., "The PHD finger of the chromatin-associated protein ING2 functions as a nuclear phosphoinositide receptor," Cell. 114(1):99-111 (2003).
Itch et at "A novel phosphatidylinositol-5-phosphate 4-kinase (phosphatidylinositol-phosphate kinase IIgamma) is phosphorylated in the endoplasmic reticulum in response to mitogenic signals," J Biol Chem. 273(32):20292-9 (1998).
Karkare et al., "RNA interference silencing the transcriptional message: aspects and applications," Appl Biochem Biotechnol. 119(1):1-12 (2004).
Lamia., "Increased insulin sensitivity and reduced adiposity in phosphatidylinositol 5-phosphate 4-kinase beta-/- mice," Mol Cell Biol. 24(11): 5080-7 (2004).

(Continued)

*Primary Examiner* — Dana Shin
(74) *Attorney, Agent, or Firm* — Kristina Bicker-Brandy; Clark & Elbing LLP

(57) ABSTRACT

The invention features methods for identifying compounds that modulate the activity of phosphatidylinositol 5-phosphate 4-kinase (PI5P4K). Inhibitors of PI5P4K can be used in, for example, the treatment or prevention of cell proliferation disorders (e.g., the prevention of tumor cell growth in p53 mutated cancers).

24 Claims, 21 Drawing Sheets

(56) References Cited

OTHER PUBLICATIONS

Nagaraj et al., "Deep proteome and transcriptome mapping of a human cancer cell line," Mol Syst Biol. 7:548. 1-8 (2011).
Nykänen et al., "Atp requirements and small interfering RNA structure in the RNA interference pathway," Cell. 107(3):309-21 (2001).
Paddison et al., "Short hairpin RNAs (shRNAs) induce sequence-specific silencing in mammalian cells," Genes Dev. 16(8):948-58 (2002).
Paddison et al., "Short hairpin activated gene silencing in mammalian cells," Methods Mol Biol. 265:85-100 (2004).
Remeh et al., "A new pathway for synthesis of phosphatidylinositol-4,5-bisphosphate," Nature. 390(6656):192-6 (1997).
Valleggi et al., "Xenon up-regulates several genes that are not up-regulated by nitrous oxide," J Neurosurg Anesthesiol. 20(4):226-32 (2008).
Vander Heiden et al., "Growth factors can influence cell growth and survival through effects on glucose metabolism," Mol Cell Biol. 21(17):5899-912 (2001).
Williams, "Role of the double-stranded RNA-activated protein kinase (PKR) in cell regulation," Biochem Soc Trans. 25(2):509-13 (1997).
International Report on Patentability for International Patent Application No. PCT/US2012/021266, dated Aug. 29, 2013 (7 pages).
Internation Search Report and Written Opinion for International Patent Application No. PCT/US2012/021266, dated Jun. 28, 2012 (11 pages).
Emerling et al., "Depletion of a putatively druggable class of phosphatidylinositol kinases inhibits growth of p53-null tumors," Cell. 155(4):844-57 (2013).
Gewinner et al., "Evidence that inositol polyphosphate 4-phosphatase type II is a tumor suppressor that inhibits PI3K signaling," Cancer Cell. 16(2):115-25 (2009).

\* cited by examiner

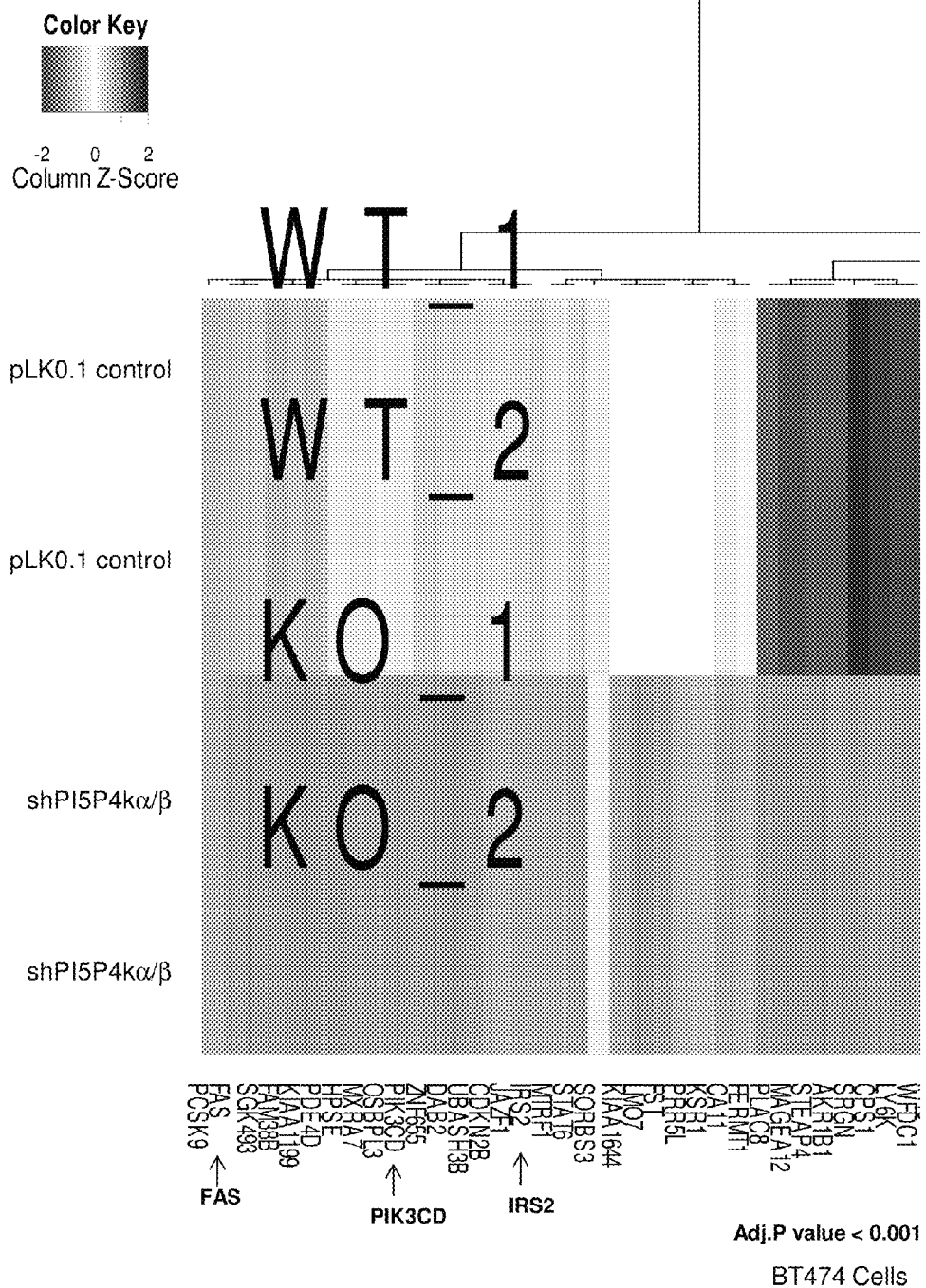

BT474 Cells

MODULATION OF PHOSPHATIDYLINOSITOL-5-PHOSPHATE-4-KINASE ACTIVITY

CROSS-REFERENCE TO RELATED APPLICATIONS

This application is the National Stage of International Application No. PCT/US2012/021266, filed Jan. 13, 2012, which claims benefit of U.S. Provisional Application No. 61/442,622, filed Feb. 14, 2011, which is hereby incorporated by reference in its entirety.

STATEMENT AS TO FEDERALLY FUNDED RESEARCH

This invention was made with government support under GM041890 awarded by NIH. The government has certain rights in the invention.

BACKGROUND OF THE INVENTION

The invention features methods for identifying compounds that modulate the activity of Type 2 phosphatidylinositol 5-phosphate 4-kinase (PI5P4K; e.g., PI5P4Kα or PI5P4Kβ). Inhibitors of PI5P4K can be used in, for example, the treatment or prevention of cell proliferation disorders (e.g., the prevention of tumor cell growth in p53 mutated cancers).

Phosphatidylinositol (PI) signaling has been shown to impact a large and diverse number of cellular processes including proliferation, survival, and cytoskeletal organization. One particular species of PI, phosphatidylinositol 5-phosphate (PI5P), has been implicated in the regulation of the tumor suppressor ING2 and the oncogene AKT. The phosphatidylinositol 5-phosphate 4-kinase (PI5P4K) family (α, β, γ isoforms) catalyzes the conversion of PI5P to PI4, 5 $P_2$. These enzymes therefore represent one means by which cells can regulate endogenous PI5P levels. Mice deficient for PI5P4Kβ (PI5P4Kβ$^{-/-}$) have been shown to exhibit enhanced insulin sensitivity and activation of AKT in skeletal muscle.

As described herein, studies using PI5P4Kα$^{-/-}$ mice and double mutant PI5P4kα$^{-/-}$β$^{-/-}$ mice indicate that complete loss of PI5P4Kα/β activity results in perinatal lethality while partial loss of PI5P4Kα/β activity leads to dramatic growth retardation. Both α and β isoforms of PI5P4K have been shown to be highly expressed in cancer cells, particularly in breast cancer cells. Based on a combination of cellular and microarray expression analyses, PI5P4K is now shown to be required for the proliferation of breast cancer cells. Further, PI5P4K deficiency restricts tumorigenesis in vivo.

The data demonstrate a critical role for PI5P4K in tumor cell growth and support a potential role in oncogenesis for PI5P4K. By inhibiting PI5P4K, a useful strategy can be developed for the prevention of tumor cell growth in p53-mutated cancers. TP53 gene is a key tumor suppressor gene and the most frequently mutated gene in human cancers. Its deletion or mutation has been found in more than 50% of human cancers, and currently more than ten million people have tumors with p53 inactive mutations. However, it has been difficult to develop drugs for targeting p53. Inhibitors for PI5P4K can be useful drugs to induce synthetic lethality of p53-mutated tumors.

Accordingly, methods for the identification of compounds that modulate PI5P4K would be useful. Further, PI5P4K inhibitor compounds that are identified according to these methods can be useful in the treatment and prevention of cancer, as well as being useful as a tool to further investigate PI5P4K function.

SUMMARY OF THE INVENTION

The invention features methods for identifying compounds that modulate the activity of phosphatidylinositol 5-phosphate 4-kinase (PI5P4K). Compounds that are identified according to these methods (e.g., PI5P4K inhibitors) can be used in methods of medical treatment (e.g., the treatment or prevention of cancer) or as tools for the further study of PI5P4K activity.

In one aspect, the invention features a method for identifying compounds that modulates phosphatidylinositol-5-phosphate-4-kinase (PI5P4K), where the method includes: (a) providing a medium including the PI5P4K and a substrate; (b) contacting the medium with a candidate compound; (c) detecting the activity of the PI5P4K; and (d) determining if the candidate compound modulates the PI5P4K. In some embodiments, the substrate is guanosine-5'-triphosphate (GTP). In further embodiments, the PI5P4K is the PI5P4Kγ isoform. In other embodiments, the substrate is adeonsine-5'-triphosphate (ATP). In further embodiments, the PI5P4K is the PI5P4Kα or PI5P4Kβ isoform.

In some embodiments, the method further includes comparing the activity detected in step (c) with the detected activity of PI5P4K in a medium not contacted with the candidate compound of step (b), where (i) increased activity of PI5P4K in the presence of the candidate compound of step (b) identifies the candidate compound as a promoter of PI5P4K activity; and (ii) where decreased activity of PI5P4K in the presence of the candidate compound of step (b) identifies the candidate compound as an inhibitor of PI5P4K activity.

In other embodiments, the method further includes comparing the activity detected in step (c) with the activity observed in a medium where the PI5P4K is absent.

In some embodiments, the medium of step (a) is a medium suitable for use in qualitative high throughput screening.

In other embodiments, the PI5P4K is the PI5P4Kα or PI5P4Kβ isoform. In other embodiments, the PI5P4K is human recombinant PI5P4K.

In certain embodiments, the medium of step (a) is a cell expressing PI5P4K. In some embodiments, the cell is a mouse embryonic fibroblast (MEF), e.g., an immortalized MEF prepared from wild-type mice. In other embodiments, the cell includes a p53 mutation. In other embodiments, the cell includes intact p53.

In some embodiments, the activity detected in step (c) is compared with the activity observed in a medium where the PI5P4K is absent.

In still other embodiments, activity detected in step (c) is the production of cellular phosphatidylinositol-5-phosphate (PI5P). In still other embodiments, the medium where the PI5P4K is absent is an immortalized MEF prepared from PI5P4kα$^{-/-}$β$^{-/-}$ knockout mice. In further embodiments, cellular PI5P levels increase compared to MEFs prepared from PI5P4kα$^{-/-}$β$^{-/-}$ knockout mice.

In some embodiments, the activity detected in step (c) is AKT activity. In certain embodiments, the AKT activity is detected using an AKT specific antibody (e.g., the phospho-T308-AKT or phospho-S473-AKT antibody).

In still other embodiments, the activity detected in step (c) is compared with the activity detected of PI5P4K in a medium not contacted with the candidate compound of (b). In some embodiments, the activity detected is step (c) is the consumption of GTP.

In certain embodiments, the PI5P4K activity is detected and optionally quantified using absorbance, fluorescence, Raman scattering, phosphorescence, luminescence, luciferase activity, or radioactivity.

In a second aspect, the invention features a compound that modulates PI5P4K. In some embodiments, the compound is identified according to the methods described herein. In some embodiments, the compound inhibits PI5P4K. In some embodiments, the compound is a nucleic acid. In some embodiments, the compound is an RNAi agent (e.g., the RNAi agent comprises a nucleic acid sequence substantially identical to the sequence of any one of SEQ ID NOs:1-16). In other embodiments, the nucleic acid specifically binds a PI5P4K peptide. In certain embodiments, the nucleic acid is a shRNA against PI5P4K. In still other embodiments, the compound selectively inhibits PI5P4K over other phosphatidylinositol phosphate kinases (PIPK) (e.g., the compound selectively inhibits PI5P4K over phosphatidylinositol-4-phosphate-5-kinase (PI4P5K) or phosphatidylinositol-3-phosphate-5-kinase (PI3P5K)). In other embodiments, the compound induces cancer cell death, reduces or prevents tumor cell growth, or inhibits cell proliferation.

In a third aspect, the invention features a method of treating cancer in a patient where the method includes administering to the patient an effective amount of a PI5P4K inhibitor, or a pharmaceutically acceptable salt or composition thereof. In some embodiments, the PI5P4K inhibitor is any compound identified according to the methods described herein. In some embodiments, the cancer is a p53 mutated cancer, e.g., lung cancer, stomach cancer, breast cancer, colon cancer, liver cancer, prostate cancer, cervical cancer, uterine cancer, head or neck cancer, esophageal cancer, ovarian cancer, bladder cancer, leukemia, or lymphoma.

In a fourth aspect, the invention features a method of inhibiting PI5P4K in a subject in need thereof, where the method includes administering to the subject an effective amount of the PI5P4K inhibitor identified according to the methods described herein. In some embodiments, the method is used for the treatment of cancer in the subject using an effective amount of any of the compounds described herein.

In a fifth aspect, the invention features a composition that includes a shRNA against a PI5P4K gene selected from the PI5P4Kα gene, the PI5P4Kβ gene, and the PI5P4Kγ gene. In some embodiments, the composition further includes GTP. In other embodiments, the composition is a pharmaceutical composition.

In a sixth aspect, the invention features a method of inhibiting, reducing, or preventing growth of a cell, where the method includes contacting the cell with any of the compositions described herein that includes a shRNA against a PI5P4K gene. In some embodiments, the cell is a cancer cell.

In a seventh aspect, the invention features a method of treating cancer in a patient, where the method includes administering to the patient an effective amount of any of the compositions described herein that includes a shRNA against a PI5P4K gene. In some embodiments, the cancer is a p53 mutated cancer, e.g., lung cancer, stomach cancer, breast cancer, colon cancer, liver cancer, prostate cancer, cervical cancer, uterine cancer, head or neck cancer, esophageal cancer, ovarian cancer, bladder cancer, leukemia, or lymphoma.

In an eighth aspect, the invention features a method of identifying a patient who may benefit from PI5PK4 antagonist therapy where the method includes (1) determining the p53 phenotype of the patient; and (2) where reduced p53 activity in the patient indicates that the patient may benefit from PI5P4K antagonist therapy. In some embodiments, the patient has a has a proliferative disorder (e.g., cancer). In other embodiments, the p53 activity is determined from proliferative tissue. In other embodiments, the method further includes administering an antagonist of PI5P4K to the patient.

By "modulating PI5P4K activity" is meant that a candidate compound alters the activity, structure, or function of PI5P4K compared to the activity, structure, or function of PI5P4K in the absence of the candidate compound. A candidate compound is considered modulate PI5P4K activity if it is shown to be a binder of PI5P4K (the binding can result in inhibition of PI5P4K activity or promotion of PI5P4K), by detecting changes in the concentration of PI5P4K present in a medium (e.g., a cell), or by detecting changes in processes (e.g., cellular processes) influenced by PI5P4K function (e.g., PI5P levels or AKT activity). PI5P4K activity can be detected using methods well known in the art, e.g., using absorbance, fluorescence, Raman scattering, phosphorescence, luminescence, luciferase activity, or radioactivity. Similarly, p53 activity can be measured by methods known in the art (for reviews, see, e.g., Goh et al., *J Pathol.* 223(2):116-26, 2011, and Brady et al., *J. Cell. Sci.* 123:2527-32; 2010).

The term an "effective amount" of an agent, as used herein, is that amount sufficient to effect beneficial or desired results, such as clinical results, and, as such, an "effective amount" depends upon the context in which it is being applied.

As used herein, a "medium" for use in the methods of the invention can include water, water based solutions, emulsions that include water, dispersions that include water, buffers, mixed water/organic solutions, a medium that can be use to culture cells, cells (e.g., mouse embryonic fibroblast cells or any the cells described herein), liposomes, pharmaceutically acceptable carriers, sterile solutions, and the like. For example, in, mixed water/organic solutions, the medium is a mixture of water and at least one other physiologically acceptable solvent chosen, for example, ethanol, DMSO, DMF, propylene glycol, alkylene glycol, or other dialkylene glycol alkyl ethers. When one or more additional physiologically acceptable solvent is present, the at least one other physiologically acceptable solvent may, for example, be present in an amount ranging from 5% to 95% by weight, relative to the total weight of the composition.

The term "pharmaceutical composition," as used herein, represents a composition formulated with a pharmaceutically acceptable excipient and including a compound (e.g., a PI5P4K inhibitor or a shRNA against a PI5P4K gene), or a pharmaceutically acceptable salt thereof, where the composition is suitable for use as part of a therapeutic regimen for the treatment of disease in a mammal. In some embodiments, the pharmaceutical composition can be manufactured or sold with the approval of a governmental regulatory agency. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other formulation described herein. Exemplary pharmaceutical compositions, including exemplary pharmaceutically acceptable excipients, are described herein.

The term "pharmaceutically acceptable salt," as use herein, represents those salts which are, within the scope of sound medical judgment, suitable for use in contact with the tissues of humans and animals without undue toxicity, irritation, allergic response and the like and are commensurate with a reasonable benefit/risk ratio. Pharmaceutically acceptable salts are well known in the art. For example, pharmaceutically acceptable salts are described in: Berge et al., J. Pharmaceutical Sciences 66:1-19, 1977 and in Pharmaceutical Salts: Properties, Selection, and Use, (Eds. P. H. Stahl and C. G. Wermuth), Wiley-VCH, 2008. Exemplary pharmaceutical salts are described herein.

By "RNAi agent" is meant any agent or compound that exerts a gene silencing effect by hybridizing a target nucleic acid. RNAi agents include any nucleic acid molecules that are capable of mediating sequence-specific RNAi (e.g., under stringent conditions), for example, a short interfering RNA (siRNA), double-stranded RNA (dsRNA), microRNA (miRNA), short hairpin RNA (shRNA), short interfering oligonucleotide, short interfering nucleic acid, short interfering modified oligonucleotide, chemically-modified siRNA, post-transcriptional gene silencing RNA (ptgsRNA), and Dicer-substrate RNA (DsiRNA). Exemplary RNAi agents include SEQ ID NOs:1-16.

Each of the terms "selectively inhibits" or "a selective inhibitor" refers to a substance that inhibits or binds PI5P4K over other phosphatidylinositol phosphate kinases (PIPK) (e.g., phosphatidylinositol-4-phosphate-5-kinase (PI4P5K) or phosphatidylinositol-3-phosphate-5-kinase (PI3P5K)), or if the substance inhibits or binds one isoform of PI5P4K (i.e., PI5P4Kα, PI5P4Kβ, or PI5P4Kγ) over one or more other isoforms. These properties can be measured by, for example, an in vitro assay. Selective inhibition can be expressed in terms of an $IC_{50}$ value or a $K_i$ value. In some embodiments, the $IC_{50}$ or $K_i$ value is 2 times lower. In still other embodiments, the $IC_{50}$ or $K_i$ value is 5, 10, 50, or even more than 100 times lower.

By "short hairpin RNA" or "shRNA" is meant a sequence of RNA that makes a tight hairpin turn and is capable of gene silencing.

By "silencing" or "gene silencing" is meant that the expression of a gene or the level of an RNA molecule that encodes one or more proteins is reduced in the presence of an RNAi agent below that observed under control conditions (e.g., in the absence of the RNAi agent or in the presence of an inactive or attenuated molecule such as an RNAi molecule with a scrambled sequence or with mismatches). Gene silencing may decrease gene product expression by, e.g., 1%, 2%, 3%, 4%, 5%, 6%, 7%, 8%, 9%, 10%, 15%, 20%, 25%, 30%, 35%, 40%, 50%, 60%, 70%, 80%, 85%, 90%, 95%, 97%, 98%, 99%, or 100% (i.e., complete inhibition).

By "substantial identity" or "substantially identical" is meant a polypeptide or polynucleotide sequence that has the same polypeptide or polynucleotide sequence, respectively, as a reference sequence, or has a specified percentage of amino acid residues or nucleotides, respectively, that are the same at the corresponding location within a reference sequence when the two sequences are optimally aligned. For example, an amino acid sequence that is "substantially identical" to a reference sequence has at least 50%, 60%, 70%, 75%, 80%, 85%, 90%, 95%, 96%, 97%, 98%, 99%, or 100% identity to the reference amino acid sequence. For polypeptides, the length of comparison sequences will generally be at least 5, 6, 7, 8, 9, 10, 11, 12, 13, 14, 15, 16, 17, 18, 19, or 20 contiguous amino acids, more preferably at least 25, 50, 75, 90, 100, 150, 200, 250, 300, or 350 contiguous amino acids, and most preferably the full-length amino acid sequence. For nucleic acids, the length of comparison sequences will generally be at least 5 contiguous nucleotides, preferably at least 10, 11, 12, 13, 14, 15, 16, 17, 18, 19, 20, 21, 22, 23, 24, or 25 contiguous nucleotides, and most preferably the full length nucleotide sequence. Sequence identity may be measured using sequence analysis software on the default setting (e.g., Sequence Analysis Software Package of the Genetics Computer Group, University of Wisconsin Biotechnology Center, 1710 University Avenue, Madison, Wis. 53705). Such software may match similar sequences by assigning degrees of homology to various substitutions, deletions, and other modifications.

By "target nucleic acid" is meant any nucleic acid sequence whose expression or activity is to be modulated. The target nucleic acid can be DNA or RNA.

As used herein, and as well understood in the art, "treatment" is an approach for obtaining beneficial or desired results, such as clinical results. Beneficial or desired results can include, but are not limited to, alleviation or amelioration of one or more symptoms or conditions; diminishment of extent of disease, disorder, or condition; stabilized (i.e., not worsening) state of disease, disorder, or condition; preventing spread of disease, disorder, or condition; delay or slowing the onset or progress of the disease, disorder, or condition; amelioration or palliation of the disease, disorder, or condition; and remission (whether partial or total), whether detectable or undetectable. For example, an effective amount of an agent can delay onset or slow progression of the disease (e.g., a cell proliferative disorder such as cancer) by leading to a reduction of a symptom of the disease (e.g., tumor size). For example, such improvements in disease symptoms can be by at least 0.1%, at least 1%, at least 5%, at least 10%, at least 25%, at least 50%, at least 75%, at least 90%, at least 95%, at least 96%, at least 97%, at least 98%, or at least 99%. "Palliating" a disease, disorder, or condition means that the extent and/or undesirable clinical manifestations of the disease, disorder, or condition are lessened and/or time course of the progression is slowed or lengthened, as compared to the extent or time course in the absence of treatment.

Other features and advantages of the invention will be apparent from the following Detailed Description, the drawings, and the claims.

BRIEF DESCRIPTION OF THE DRAWINGS

FIG. 5A shows tumor formation over time in nude mice injected with the BT474 cancer cell line expressing shRNA control or shRNA PI5P4Kα/β. FIG. 5B shows tumor growth in mice (shPI5P4Kα/β (right flank) or pLK0.1 control cells (left flank)). FIG. 5C shows pictures of tumors after mice were euthanized. shPI5P4Kα/β (bottom) and pLK0.1 control cells (top).

FIG. 7A shows the heat map of differentially expressed genes with adjusted p value <0.001. FIGS. 7B and 7C show the Gene Set Enrichment Analysis (GSEA) and KEGG pathway analysis of gene set (shPI5P4Kα/β vs. pLK0.1 control). Enrichment plot titled BRCA_PROGNOSIS_POS in FIG. 7B shows +ve cor with prognosis: genes whose expression is consistently positively correlated with breast cancer outcomes (higher expression is associated with good prognosis). Enrichment plot titled BRCA_BRCA1_NEG in FIG. 7B shows −ve cor with BRCA1 signature: genes whose expression is consistently negatively correlated with brca1 germline status in breast cancer—higher expression is associated with BRCA1 tumors. Enrichment plot titled CELL_CYCLE_ARREST in FIG. 7B shows +ve cor with cell cycle arrest: genes annotated by the GO term GO:0007050. Any process by which progression through the cell cycle is halted during one of the normal phases (G1, S, G2, M).

DETAILED DESCRIPTION OF THE INVENTION

Figure 1:
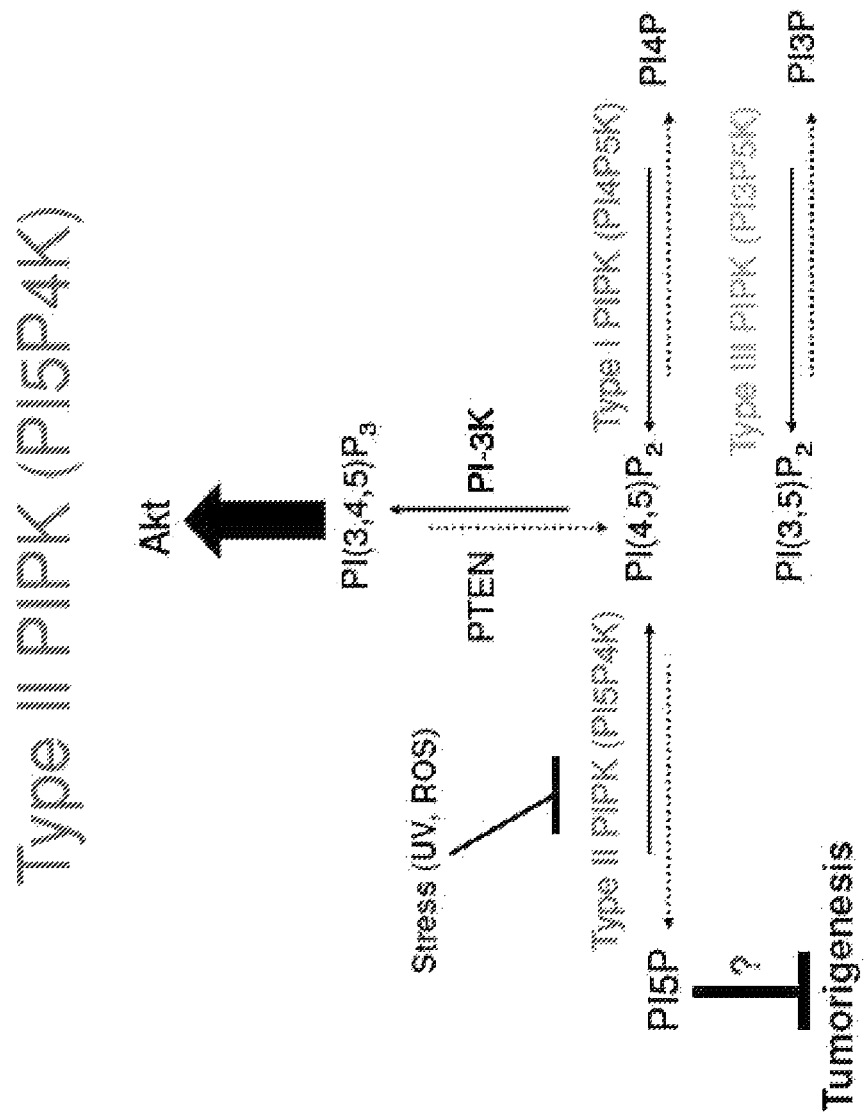
FIG. 1 shows a schematic diagram of PI5P4K signaling. The scheme shows the type II phosphatidylinositol 5-phosphate 4-kinase (PI5P4K) family (α, β, and γ) isoforms) that catalyzes the conversion of PI5P to PI4, 5 P2.

The invention described herein features a screening method for the identification of modulators of PI5P4K activity.

The phosphoinositide family includes seven derivatives of phosphatidylinositol (PI) that are formed through the phosphorylation of the 3-, 4-, and 5-positions on the inositol ring. Phosphoinositides have distinct biologically roles and regulate many cellular processes, including proliferation, survival, glucose uptake, and migration. Phosphoinositide kinases, phosphatases, and phospholipases spatially and temporally regulate the generation of the different phosphoinositide species, which localize to different subcellular compartments. Phosphatidylinositol-3,4,5-trisphosphate (PI-3,4,5-$P_3$) is synthesized by phosphoinositide 3-kinase (PI3K) and is an essential lipid that serves as the plasma membrane docking sites for proteins that have pleckstrin-homology (PH) domains, including AKT. The serine/threonine kinase AKT (also known as protein kinase B or PKB) is a proto-oncogene that has critical regulatory roles in insulin signaling and cancer progression. Further, PI signaling has been implicated in a number of cellular processes (see below).

Phosphatidylinositol-4,5-bisphosphate (also referred to as PI-4,5-$P_2$) is the major substrate for Class I PI3Ks and has a significant role itself in mediating the localization of proteins to the plasma membrane and in nucleating cortical actin polymerization. Until 1997, it was thought that PI-4, 5-$P_2$ was produced exclusively by phosphorylation of phosphatidylinositol-4-phosphate (PI-4-P) at the 5 position of the inositol ring, a reaction catalyzed by the Type 1 PI-4-P 5-kinases (PIP5K1A, B and C). Subsequently, a second highly-related family of PIP kinases (the Type 2 PIP kinases) were found to produce PI-4,5-$P_2$ by phosphorylating the 4 position of phosphatidylinositol-5-phosphate (PI-5-P), a contamination in commercial PI-4-P isolated from bovine brain. This led to the discovery of PI-5-P, a lipid that had been previously overlooked due to its co-migration with the much more abundant PI-4-P (Rameh et al., *Nature* 390:192, 1997). The Type 2 PIP kinases are not present in yeast but are conserved in higher eukaryotes from worms and flies to mammals. The bulk of PI-4,5-$P_2$ in most tissues is likely derived from the Type 1 PIP5Ks, yet recent quantitative proteomic studies on cell lines have revealed a higher abundance of PI5P4Ks than PI4P5Ks (Nagaraj et al., *Mol. Syst. Biol.*, doi:10.1038/msb.2011.81, published online Nov. 8, 2011).

Expression of PI5P4K in cancer cells appears critical for tumor cell growth and proliferation in vivo. In addition, the loss of PI5P4K in p53 deficient mice prevents the onset of cancer. Moreover, PI5P4Kβ$^{-/-}$ p53$^{-/-}$ animals are embryonic lethal, indicating the tight linkage between p53 status and PI5P4K. These findings indicate that PI5P4K represents a target for drug development, particularly in p53-mutated cancers, that would enable the inhibition of proliferation in a relatively tumor-specific manner. Accordingly, compounds that inhibit PI5P4K may be useful for the treatment of cell proliferative disorders (e.g., p53 mutated cancers), as well as any other diseases that benefit from the inhibition of PI5P4K.

As shown in the examples herein, high levels of both PI5P4Kα and PI5P4Kβ enzymes are found in a number of breast cancer cell lines. Further, amplification of the PIP4K2B gene and high levels of both the PI5P4Kα and PI5P4Kβ proteins in a subset of human breast tumors are also shown. Additionally, knockdown of the levels of both PI5P4Kα and PI5P4Kβ in a TP53 deficient breast cancer cell line blocked growth on plastic and in xenografts. Additional experiments employed mice having germ-line deletions of PIP4K2A and PIP4K2B and which were crossed with TP53$^{-/-}$ mice. Tumor formation was then evaluated in all the viable genotypes. It was found that mice with homozygous deletion of both TP53 and PIP4K2B were not viable, indicating a synthetic lethality for loss of these two genes. Importantly, mice with the genotype PIP4K2A$^{-/-}$, PIP4KB$^{+/-}$, TP53$^{-/-}$ were viable and had a dramatic reduction in tumor formation compared to siblings that were TP53$^{+/+}$ and wild type for PIP4K2B and/or PIP4K2A genes. These results shown that PI5P4Kα and PI5P4Kβ can be targets for pharmaceutical intervention in cancers that are defective in TP53.

Phosphatidylinositol (PI) Signaling

Phosphatidylinositol (PI) signaling has been shown to impact a large and diverse number of cellular processes including proliferation, survival, and growth, and dysregulation of this process has been shown in cancer and other diseases (Cantley, *Science,* 296:1655, 2002). Phosphatidylinositol 5-phosphate (PI5P) has been shown to be involved in the regulation of the oncogene AKT (Carricaburu et al., PNAS 100:9867, 2003; Lamia et al., *Mol. Cell. Biol.* 24:5080, 2004). PI5P also has been shown to regulate the tumor suppressor ING2 (Gozani et al., *Cell,* 114:99, 2003).

The type II phosphatidylinositol 5-phosphate 4-kinase (PI5P4K) family (α, β, γ isoforms) catalyzes the conversion of PI5P to PI4, 5 P2 (Rameh et al., *Nature* 390:192, 1997) (FIG. 1). Alternatively, PI4, 5 P2 can also be synthesized through phosphatidylinositol-4-phosphate (PI4P) by the type I phosphatidylinositol 4-phosphate 5-kinases (PI4P5K) (FIG. 1). These PI5P4K enzymes therefore represent one means by which cells can regulate endogenous PI5P levels, and studies have shown that the enzymes have important roles in insulin signaling and in stress responses. For example, mice deficient for PI5P4Kβ (PI5P4Kβ−/−) exhibit enhanced insulin sensitivity and activation of AKT in skeletal muscle (Lamia et al., *Mol. Cell. Biol.* 24:5080, 2004). Cellular stresses, such as UV and $H_2O_2$, have been shown to increase PI5P levels via inhibition of PI5P4Kβ (Jones et al., *Mol. Cell.* 23:685, 2006). This occurs through the direct phosphorylation of PI5P4Kβ at Ser326 by the p38-stress activated protein kinase (ibid.). In studies with PI5P4Kα−/− mice and double mutant PI5P4kα−/−β−/− mice, complete loss of PI5P4Kα/β activity results in perinatal lethality while partial loss of PI5P4Kα/β activity leads to dramatic growth inhibition in cells (see, e.g., Example 1 described herein).

Regulation of Cellular Proliferation by Modulating PI5P4K

As described herein, type II phosphatidylinositol 5-phosphate 4-kinase (PI5P4K) is shown to have a central role in regulating cellular proliferation. More specifically, by inhibiting PI5P4K, tumor cell growth in p53-mutated cancers can be prevented. TP53 gene is a key tumor suppressor gene and the most frequently mutated gene in human cancers; its deletion or mutation has been found in more than 50% of human cancers. Currently, more than ten million people have tumors with p53 inactive mutations.

Little is known about the role of PI5P4K in cancer, except that both α and β isoforms have been shown to be highly expressed in cancer cells, particularly in breast cancer cells. As shown herein, the inhibition of PI5P4K selectively inhibits cell proliferation of p53-mutated cancer cells and can provide an effective strategy for targeting p53-mutated cancers. Further, inhibitors for PI5P4K can be useful drugs to induce synthetic lethality of p53-mutated tumors. Accordingly, the discovery that PI5P4K can inhibit p53-mutated tumor cell can lead to new methods for the treatment of cancers with p53 mutations.

PI5P4K Silencing Using RNA Interference

As shown herein, experiments using short hairpin RNA (shRNA), constructs directed against the PI5P4Kα and β genes have shown that decreased PI5PK4 expression is accompanied by an increase in PI5P levels and an inhibition of cell proliferation in p53 null breast cancer cells (Example 1). In addition to shRNA constructs, other RNAi agent may be used to exerts a gene silencing effect by way of an RNA interference (RNAi) pathway. Exemplary RNAi agents include SEQ ID NOs:1-16.

The term "RNAi" is used herein to refer collectively to several gene silencing techniques, including the use of siRNA (short interfering RNAs), shRNA (short hairpin RNA: an RNA bearing a fold-back stem-loop structure), dsRNA (double-stranded RNA; see, for example, Williams, Biochem. Soc. Trans. 25:509, 1997; Gil and Esteban, Apoptosis 5:107, 2000; Clarke and Mathews, RNA 1:7, 1995; Baglioni and Nilsen, Interferon 5:23, 1983), miRNA (micro RNAs), stRNAs (short (or "small") temporal RNAs), and the like, all of which can be used in the methods of the present invention. A number of methods for producing and selecting RNAi molecules, such as shRNAs, siRNAs, and dsRNAs, have been developed and can be used in the present invention (see, e.g., Paddison et al., Methods Mol. Biol. 265:85, 2004; and Kakare et al., Appl. Biochem. Biotechnol. 119:1, 2004). In addition, commercially available kits can be used to make RNAi for use in the methods of the invention (e.g., GeneEraser™ (catalog #240090) from Stratagene, La Jolla, Calif.).

Molecules for effecting RNA interference (herein termed RNAi)-based strategies can be employed to explore PI5P4K gene function, as a basis for therapeutic drug design, as well as to treat diseases that benefit from modulation of PI5P4K activity. These strategies are based on the principle that sequence-specific suppression of gene expression (via transcription or translation) can be achieved by intracellular hybridization between genomic DNA or mRNA and a complementary antisense species. The formation of a hybrid RNA duplex interferes with transcription of the target PI5P4K-encoding genomic DNA molecule, or processing, transport, translation, or stability of the target PI5P4K mRNA molecule.

RNAi strategies can be delivered by a variety of approaches. For example, antisense oligonucleotides or antisense RNA can be directly administered (e.g., by intravenous injection) to a subject in a form that allows uptake into cells. Alternatively, viral or plasmid vectors that encode antisense RNA (or antisense RNA fragments) can be introduced into a cell in vivo or ex vivo. RNAi effects can be induced by control (sense) sequences; however, the extent of phenotypic changes is highly variable. Phenotypic effects induced by antisense molecules are based on changes in criteria such as protein levels, protein activity measurement, and target mRNA levels.

PI5P4K gene therapy can also be accomplished by direct administration of antisense PI5P4K mRNA to a cell that is expected to be adversely affected by the expression of wild type or mutant PI5P4K. The antisense PI5P4K mRNA can be produced and isolated by any standard technique. Administration of antisense PI5P4K mRNA to cells can be carried out by any of the methods for direct nucleic acid molecule administration described above.

PI5P4K can be used as guide sequences in the design of RNAi molecules of the invention, which can include sense and/or antisense sequences or regions that are generally covalently linked by nucleotide or non-nucleotide linker molecules, as is known in the art. Alternatively, the linkages can be non-covalent, involving, for example, ionic, hydrogen bonding, Van der Waals, hydrophobic, and/or stacking interactions. siRNAs of the invention can be, e.g., between 19 and 29 nucleotides in length, while dsRNAs can be at least 30, 50, 100, or 500 nucleotides in length. As is known in the art, shRNAs are generally designed to form double-stranded regions of 19 to 29 nucleotides in length, although these lengths can vary (see Paddison et al., Genes Dev. 16:948, 2002). Exemplary requirements for siRNA length, structure, chemical composition, cleavage site position, and sequences essential to mediate efficient RNAi activity are described, for example, by Elbashir et al., EMBO J. 20:6877, 2001; and Nykanen et al., Cell 107:309, 2001.

RNAi molecules of the present invention include any form of RNA, such as partially purified RNA, essentially pure RNA, synthetic RNA, recombinantly produced RNA, as well as RNA that differs from naturally occurring RNA by the addition, deletion, substitution, and/or alteration of one or more nucleotides. Such alterations can include the addition of non-nucleotide material to, e.g., the end(s) of the RNA or internally (at one or more nucleotides of the RNA), or the RNA molecule can contain a 3' hydroxyl group. RNAi molecules of the present invention can also include non-standard nucleotides, including non-naturally occurring nucleotides or deoxyribonucleotides. Examples of modified nucleotides that can be included in RNAi molecules of the invention, such as 2'-O-methyl ribonucleotides, 2'-deoxy-2'-fluoro ribonucleotides, "universal base" nucleotides, 5-C-methyl nucleotides, nucleotides with phosphorothioate internucleotide linkages, and inverted deoxyabasic residues, are described, for example, in U.S. Patent Application Publication No. 20040019001. RNAi molecules directed against PI5P4K can be used individually, or in combination with other RNAi constructs, for example, constructs against heart of glass (heg).

The RNAi agents (e.g., shRNAs and SEQ ID NOs:1-16) used in the invention are at least 10 nucleotides, preferably 11, 12, 13, 14, 15, 16, 17, 18, 19, 20, 21, 22, 23, 24, 25, 26, 27, 28, 29, 30, 31, 32, 33, 34, or 35 nucleotides in length and even up to 50 or 100 nucleotides in length (inclusive of all integers in between). For example, such small RNAs that are substantially identical to or complementary to any region of a polypeptide described herein are included in the invention. Non-limiting examples of small RNAs are substantially identical to (e.g., 60%, 65%, 70%, 75%, 80%, 85%, 90%, 95%, 96%, 97%, 98%, 99%, or 100% sequence identity) or complementary to the PI5P4K nucleic acid sequence. Use of the RNAi agents (e.g., shRNAs) can result in at least 1, 5, 10, 15, 20, 25, 30, 35, 40, 45, 50, 55, 60, 65, 70, 75, 80, 85, 90, 95, 96, 97, 98, or 99% activity. In some embodiments, the RNAi agent may result in complete silence of the gene.

shRNA Constructs shRNAs can be used in the methods of the invention. shRNAs are designed such that both the sense and antisense strands are included within a single RNA molecule and connected by a loop of nucleotides. shRNAs can be synthesized and purified using standard in vitro T7 transcription synthesis. shRNAs can also be subcloned into an expression vector, which can then be transfected into cells and used for in vivo expression of the shRNA. shRNAs preferably form double-stranded regions of 19 to 29 nucleotides in length, e.g., 22 to 29 nucleotides 25 to 29 nucleotides in length, or even 29 nucleotides in length.

A variety of methods are available for transfection of dsRNA into mammalian cells. For example, there are several commercially available transfection reagents useful for lipid-based transfection of siRNAs including, but not limited to, TransIT-TKOT™ (Mirus), Transmessenger™ (Qiagen), Oligofectamine™ and Lipofectamine™ (Invitrogen), siPORTT™ (Ambion), and DharmaFECT™ (Fisher Scientific). Agents are also commercially available for electroporation-based methods for transfection of siRNA, such as siPORTer™ (Ambion). Microinjection techniques may also be used. The small RNA can also be transcribed from an expression construct introduced into the cells, where the expression construct includes a coding sequence for transcribing the small RNA operably linked to one or more transcriptional regulatory sequences. Where desired, plasmids, vectors, or viral vectors can also be used for the delivery of dsRNA or siRNA, and such vectors are known in the art. Protocols for each transfection reagent are available from the manufacturer. Additional methods are known in the art and are described, for example, in U.S. Patent Application Publication No. 2006/0058255.

PI5P4K Modulators as Research Tools

PI5P4K Modulators (e.g., chemical inhibitors of PI5P4K) can serve as valuable research tools to dissect the impact of PI5P4K activity and its regulation on both cell signaling and proliferation. There is currently a deficiency of compounds in the PI5P4K field that can be used to study the function of this kinase. By contrast, there has been a massive expansion in investigating the function and role of PI3K after the discovery of the PI3K inhibitors, wortamannin, and LY294002. In view of the importance of PI5P4K in insulin signaling and tumorigenesis, the use of compounds that modulate the activity of PI5P4K will highlight the significance of this kinase.

PI5P4K Isoforms, Substrates, and Use in Screening Methods

As described herein in Example 3, the PI5P4Kα isoform is shown to equally utilize both ATP and GTP, while the PI5P4Kβ isoform favors GTP over ATP. Moreover, the PI5P4Kγ isoform, which had been shown to be a dead kinase, is now shown to have activity with GTP. This latter finding can be used in methods for identifying modulators of PI5P4K modulators (i.e., inhibitors or activators of PI5P4K) with the right substrate, GTP.

Thus far almost all kinases are known to use ATP as its substrate. Therefore, it is unusual that the PI5P4K isoforms have distinctive GTP-utilization for their activity. When ATP is used as a substrate, one may not be able to assess compounds or probes against the kinase activity of PI5P4K isoforms. Accordingly, this finding of distinctive GTP-utilization of PI5P4Ks will be key in methods to identify compounds that modulate PI5P4K.

PI5P4K for use in the screening methods may be produced by any method known in the art for expression of recombinant proteins. An exemplary method is described in Demian et al., *Journal of Biomolecular Screening*, 14(7); 2009. PI5P4K sequences of each of the α, β, and γ are known to the skilled artisan. For example, Table 1 provides references for the sequence of human PI5P4K, each of which is hereby incorporated by reference.

TABLE 1

| Isoform | NCBI Accession Number | No. of amino acids in Protein |
| --- | --- | --- |
| PI5P4Kβ | P78356.1 | 416 aa protein |
| PI5P4Kα | P48426.2 | 406 aa protein |
| PI5P4Kγ | Q8TBX8.3 | 421 aa protein |
| PI5P4Kβ | NP_003550.1 | 416 aa protein |
| PI5P4Kγ | NP_001139732.1 | 373 aa protein |
| PI5P4Kγ | NP_001139730 | 421 aa protein |
| PI5P4Kγ | NP_079055.3 | 421 aa protein |
| PI5P4Kγ | NP_001139731.1 | 403 aa protein |
| PI5P4Kα | NP_005019.2 | 406 aa protein |
| PI5P4Kα | AAH18034.1 | 406 aa protein |
| PI5P4Kγ | AAH28596.1 | 421 aa protein |
| PI5P4Kβ | AAH27459.1 | 281 aa protein |

The activity of PI5P4K can be detected using a number of methods known in the art. For example, the activity can be detected and/or measured e.g., monitoring the concentration of a compound (e.g., GTP) present in the reaction mixture. Other methods for detecting or quantifying PI5P4K activity can use absorbance, fluorescence, Raman scattering, phosphorescence, luminescence, luciferase activity, or radioactivity.

Methods for detecting or quantifying the activity of PI5P4K the amount can employ, for example, absorbance, fluorescence, Raman scattering, phosphorescence, luminescence, luciferase assays, and radioactivity.

Candidate compounds may be chosen if they, for example, demonstrate inhibition of PI5P4K greater than 10, 15, 20, 25, 30, 35, 40, 45, 50, 55, 60, 65, 70, 75, 80, 85, 90, 95, 99, or 99.9%.

Therapy

PI5P4K inhibitors can be useful in the treatment of proliferative disorders such as cancer. For example, PI5P4K inhibitors can be used in the treatment of p53 mutated cancers. When PI5P4K inhibitors are used in therapy, the therapy may be performed alone or in combination with another therapy (e.g., surgery, radiation therapy, chemotherapy, immunotherapy, anti-angiogenesis therapy, or gene therapy). The duration of the combination therapy depends on the type of disease or disorder being treated, the age and condition of the patient, the stage and type of the patient's disease, and how the patient responds to the treatment. Therapy may be given in on-and-off cycles that include rest periods.

Cancer and Other Proliferative Disorders

PI5P4K inhibitors can be used in the treatment of, e.g., cancer. Cancers include, without limitation, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma).

Proliferative disorders include, e.g., cancer (e.g., benign and malignant), benign prostatic hyperplasia, psoriasis, abnormal keratinization, lymphoproliferative disorders (e.g., a disorder in which there is abnormal proliferation of cells of the lymphatic system), chronic rheumatoid arthritis, arteriosclerosis, restenosis, diabetic retinopathy, and neurodegenerative disorders. Proliferative disorders are described in U.S. Pat. Nos. 5,639,600 and 7,087,648, hereby incorporated by reference.

p53 Mutated Cancers

The p53 gene is a key tumor suppressor gene and the most frequently mutated gene in human cancers. Its deletion or mutation has been found in more than 50% of human cancers; currently, more than ten million people have tumors with p53 inactive mutations. The discovery that inhibition of PI5P4K selectively inhibits cell proliferation of p53-mutated cancer cells can provide a new strategy for targeting p53-mutated cancers. Inhibitors for PI5P4K may be effective drugs to induce synthetic lethality of p53-mutated tumors. Exemplary p53 mutated cancer include lung cancer, stomach cancer, breast cancer, colon cancer, liver cancer, prostate cancer, cervical cancer, uterine cancer, head or neck cancer, esophageal cancer, ovarian cancer, bladder cancer, leukemia, and lymphoma Additional Therapeutic Regimens If desired, additional therapeutic regimens may be provided along with the compounds described herein. For example, therapeutic agents may be administered with PI5P4K inhibitors at concentrations known to be effective for such therapeutic agents. Particularly useful agents include, e.g., antimicrobial agents, anti-inflammatory agents, antiviral agents, antifungal agents, analgesics, anesthetics, sedatives, lubricants, immunomodulatory agents, and 5-aminosalicylate derivatives.

If more than one agent is employed, therapeutic agents may be delivered separately or may be admixed into a single formulation. When agents are present in different pharmaceutical compositions, different routes of administration may be employed. Routes of administration include, e.g., ocular, inhalation, parenteral, dermal, transdermal, buccal, rectal, sublingual, perilingual, nasal, topical administration, or oral administration. Parenteral administration includes intravenous, intraperitoneal, subcutaneous, and intramuscular administration.

PI5P4K inhibitors may be admixed with additional active or inert ingredients, e.g., in conventional pharmaceutically acceptable carriers. A pharmaceutical carrier can be any compatible, non-toxic substance suitable for the administration of the compositions of the present invention to a patient. Pharmaceutically acceptable carriers include, for example, water, saline, buffers and other compounds, described, for example, in the Merck Index, Merck & Co., Rahway, N.J. Slow release formulations or a slow release apparatus may be also be used for continuous administration.

In addition to the administration of therapeutic agents, the additional therapeutic regimen may involve other therapies, including modification to the lifestyle of the subject being treated.

Formulation of Pharmaceutical Compositions

Administration of PI5P4K inhibitors may be by any suitable means that results in a concentration of the compound that is effective in treating the disease associated with PI5P4K inhibitors. The compound may be contained in any appropriate amount in any suitable carrier substance. The composition may be provided in a dosage form that is suitable for the oral, parenteral (e.g., intravenous or intramuscular), rectal, cutaneous, nasal, vaginal, inhalant, skin (e.g., a patch), ocular, or intracranial administration route. Thus, the composition may be in the form of, e.g., tablets, capsules, pills, powders, granulates, suspensions, emulsions, solutions, gels including hydrogels, pastes, ointments, creams, plasters, drenches, osmotic delivery devices, suppositories, enemas, injectables, implants, sprays, or aerosols. The pharmaceutical compositions may be formulated according to conventional pharmaceutical practice (see, e.g., Remington: *The Science and Practice of Pharmacy*, 20th edition, 2000, ed. A. R. Gennaro, Lippincott Williams & Wilkins, Philadelphia, and Encyclopedia of *Pharmaceutical Technology*, eds. J. Swarbrick and J. C. Boylan, 1988-1999, Marcel Dekker, New York).

Pharmaceutical compositions that include PI5P4K inhibitors may be formulated to release the active compound immediately upon administration or at any predetermined time or time period after administration. The latter types of compositions are generally known as controlled release formulations, which include (i) formulations that create substantially constant concentrations of the agent(s) of the invention within the body over an extended period of time; (ii) formulations that after a predetermined lag time create substantially constant concentrations of the agents of the invention within the body over an extended period of time; (iii) formulations that sustain the agent(s) action during a predetermined time period by maintaining a relatively constant, effective level of the agent(s) in the body with concomitant minimization of undesirable side effects associated with fluctuations in the plasma level of the agent(s) (sawtooth kinetic pattern); (iv) formulations that localize action of agent(s), e.g., spatial placement of a controlled release composition adjacent to or in the diseased tissue or organ; (v) formulations that achieve convenience of dosing, e.g., administering the composition once per week or once every two weeks; and (vi) formulations that target the action of the agent(s) by using carriers or chemical derivatives to deliver the combination to a particular target cell type. Administration of the combination in the form of a controlled release formulation is especially preferred for compounds having a narrow absorption window in the gastro-intestinal tract or a relatively short biological half-life.

Any of a number of strategies can be pursued in order to obtain controlled release in which the rate of release outweighs the rate of metabolism of the compound in question. In one example, controlled release is obtained by appropriate selection of various formulation parameters and ingredients, including, e.g., various types of controlled release compositions and coatings. Thus, the combination is formulated with appropriate excipients into a pharmaceutical composition that, upon administration, releases the combination in a controlled manner. Examples include single or multiple unit tablet or capsule compositions, oil solutions, suspensions, emulsions, microcapsules, molecular complexes, microspheres, nanoparticles, patches, and liposomes.

Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Nanoparticulate formulations (e.g., biodegradable nanoparticles, solid lipid nanoparticles, and liposomes) may be used to control the biodistribution of the compounds. Other potentially useful parenteral delivery systems include ethylene-vinyl acetate copolymer particles, osmotic pumps, implantable infusion systems, and liposomes.

Formulations for inhalation may contain excipients or may be aqueous solutions containing, for example, polyoxyethylene-9-lauryl ether, glycholate and deoxycholate, or may be oily solutions for administration in the form of nasal drops, or as a gel. The concentration of the compound in the formulation will vary depending upon a number of factors, including the dosage of the drug to be administered, and the route of administration.

Formulations for oral use include tablets containing the active ingredient(s) in a mixture with non-toxic pharmaceutically acceptable excipients. These excipients may be, for example, inert diluents or fillers (e.g., sucrose and sorbitol), lubricating agents, glidants, and antiadhesives (e.g., magnesium stearate, zinc stearate, stearic acid, silicas, hydrogenated vegetable oils, or talc). Formulations for oral use may also be provided in unit dosage form as chewable tablets, tablets, caplets, or capsules (e.g., as hard gelatin capsules wherein the active ingredient is mixed with an inert solid diluent or as soft gelatin capsules wherein the active ingredient is mixed with water or an oil medium).

The compound may be optionally administered as a pharmaceutically acceptable salt, such as, e.g., a non-toxic acid addition salt or metal complex that is commonly used in the pharmaceutical industry. Examples of acid addition salts include, e.g., organic acids (e.g., acetic, lactic, pamoic, maleic, citric, malic, ascorbic, succinic, benzoic, palmitic, suberic, salicylic, tartaric, methanesulfonic, toluenesulfonic, or trifluoroacetic acids), polymeric acids (e.g., tannic acid or carboxymethyl cellulose), and inorganic acids (e.g., hydrochloric acid, hydrobromic acid, sulfuric acid, or phosphoric acid). Metal complexes include, e.g., zinc and iron complexes.

The formulations can be administered to human subjects in therapeutically effective amounts. Typical dose ranges are from about 0.01 µg/kg to about 2 mg/kg of body weight per day. The preferred dosage of drug to be administered is likely to depend on such variables as the type and extent of the disorder, the overall health status of the particular subject, the specific compound being administered, the excipients used to formulate the compound, and its route of administration. Standard clinical trials maybe used to optimize the dose and dosing frequency for any particular compound.

EXAMPLES

The following examples are put forth so as to provide those of ordinary skill in the art with a complete disclosure and description of how the methods and compounds claimed herein are performed, made, and evaluated, and are intended to be purely exemplary of the invention and are not intended to limit the scope of what the inventors regard as their invention.

As shown in the examples below, a subset of breast cancers express high levels of PI5P4Kα and β, in some cases due to amplification of the gene encoding the β isoform (PIP4K2B). Knocking down PI5P4Kα and β in a TP53 deficient human breast cancer cell line caused activation of AKT. This knockdown resulted in impaired growth on plastic and in xenografts and is consistent with oncogenic stress-induced senescence.

To study the importance of PI5P4Kα and β for tumor formation in vivo, mice were generated with germ-line deletions of the genes encoding these two enzymes and crossed these mice with TP53$^{-/-}$ mice. Although mice lacking both alleles of PIP4K2B were viable with a normal lifespan, mice of the genotype PIP4K2B$^{-/-}$, TP53$^{-/-}$ were not viable. Further, mice of the genotype PIP4K2A$^{-/-}$, PIP4K2B$^{+/-}$, TP53$^{-/-}$ were viable and had a dramatic reduction in tumor formation compared to TP53$^{-/-}$ littermates. These results indicate that combined loss of PIP4K2B and TP53 results in lethality and that inhibitors of PI5P4Ks can be effective in preventing or treating cancers with mutations in TP53.

All lentiviral vectors were obtained from Broad Institute TRC shRNA library, including the following shown in Table 2.

TABLE 2

Entry Sequence Information

A    PI5P4Kα pLK0.1 shRNA sequence 1 (human; Clone ID = TRCN0000006009)

Target Sequence: CCTCGGACAGACATGAACATT (SEQ ID NO: 1)

Hairpin Sequence:
5'-CCGG-CCTCGGACAGACATGAACATT-CTCGAG-AATGTTCATGTCTGTCCGAGG-TTTTT-3'
(SEQ ID NO: 2)

Oligo design for arrayed cloning:
Forward sequence:
5'-CCGGCCTCGGACAGACATGAACATTCTCGAGAATGTTCATGTCTGTCCGAGGTTTTTG-3'
(SEQ ID NO: 3)

Reverse sequence:
5'-AATTCAAAAACCTCGGACAGACATGAACATTCTCGAGAATGTTCATGTCTGTCCGAGG-3'
(SEQ ID NO: 4)

B    PI5P4Kα pLK0.1 shRNA sequence 2 (human; Clone ID = TRCN0000006010)

Target Sequence: CGGCTTAATGTTGATGGAGTT (SEQ ID NO: 5)

Hairpin Sequence:
5'-CCGG-CGGCTTAATGTTGATGGAGTT-CTCGAG-AACTCCATCAACATTAAGCCG-TTTTT-3'
(SEQ ID NO: 6)

Oligo design for arrayed cloning:
Forward sequence:
5'-CCGGCGGCTTAATGTTGATGGAGTTCTCGAGAACTCCATCAACATTAAGCCGTTTTTG-3'
(SEQ ID NO: 7)

Reverse sequence:
5'-AATTCAAAAACGGCTTAATGTTGATGGAGTTCTCGAGAACTCCATCAACATTAAGCCG-3'
(SEQ ID NO: 8)

C    PI5P4Kβ pLK0.1 shRNA sequence 1 (human; Clone ID = TRCN0000006013)

Target Sequence: CCCTCGATCTATTTCCTTCTT (SEQ ID NO: 9)

Hairpin Sequence:
5'-CCGG-CCCTCGATCTATTTCCTTCTT-CTCGAG-AAGAAGGAAATAGATCGAGGG-TTTTT-3'
(SEQ ID NO: 10)

Oligo design for arrayed cloning:
Forward sequence:
5'-CCGGCCCTCGATCTATTTCCTTCTTCTCGAGAAGAAGGAAATAGATCGAGGGTTTTTG-3'
(SEQ ID NO: 11)

Reverse sequence:
5'-AATTCAAAAACCTCGATCTATTTCCTTCTTCTCGAGAAGAAGGAAATAGATCGAGGG-3'
(SEQ ID NO: 10)

D    PI5P4Kβ pLK0.1 shRNA sequence 2 (human; Clone ID = TRCN0000006017)

Target Sequence: CAAACGCTTCAACGAGTTTAT (SEQ ID NO: 13)

Hairpin Sequence:
5'-CCGG-CAAACGCTTCAACGAGTTTAT-CTCGAG-ATAAACTCGTTGAAGCGTTTG-TTTTT-3'
(SEQ ID NO: 14)

Oligo design for arrayed cloning:
Forward sequence:
5'-CCGGCAAACGCTTCAACGAGTTTATCTCGAGATAAACTCGTTGAAGCGTTTGTTTTTG-3'
(SEQ ID NO: 15)

Reverse sequence:
5'-AATTCAAAAACAAACGCTTCAACGAGTTTATCTCGAGATAAACTCGTTGAAGCGTTTG-3'
(SEQ ID NO: 16)

The pLK0.1 vector was used as the control. To generate virus using the above described transfer vector, pMD2.G (Addgene plasmid 12259) and psPAX2 (Addgene plasmid 12260) were used.

Example 1

Figure 2A:
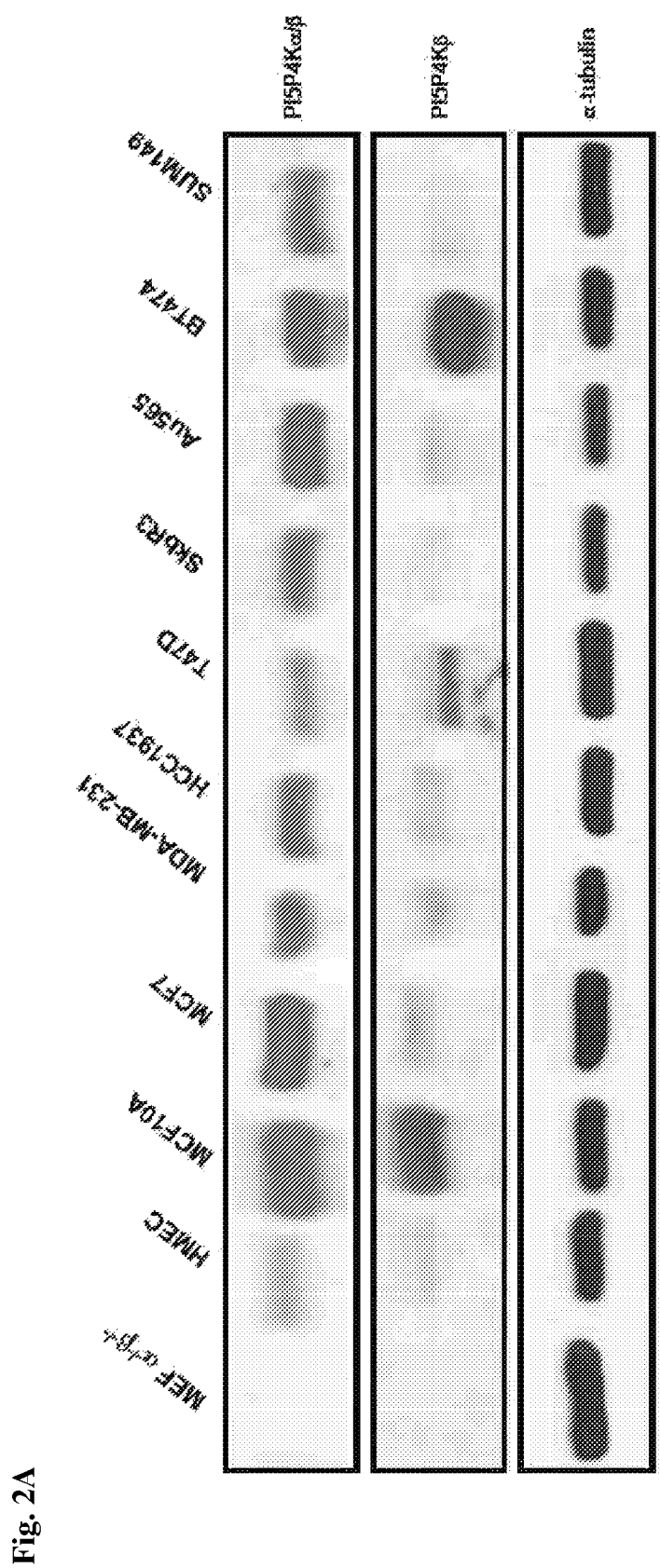
FIG. 2A shows PI5P4Kα/β expression in a panel of breast cancer cell lines. In these experiments, an anti-α tublin antibody was used as the loading control.
Figure 2B:
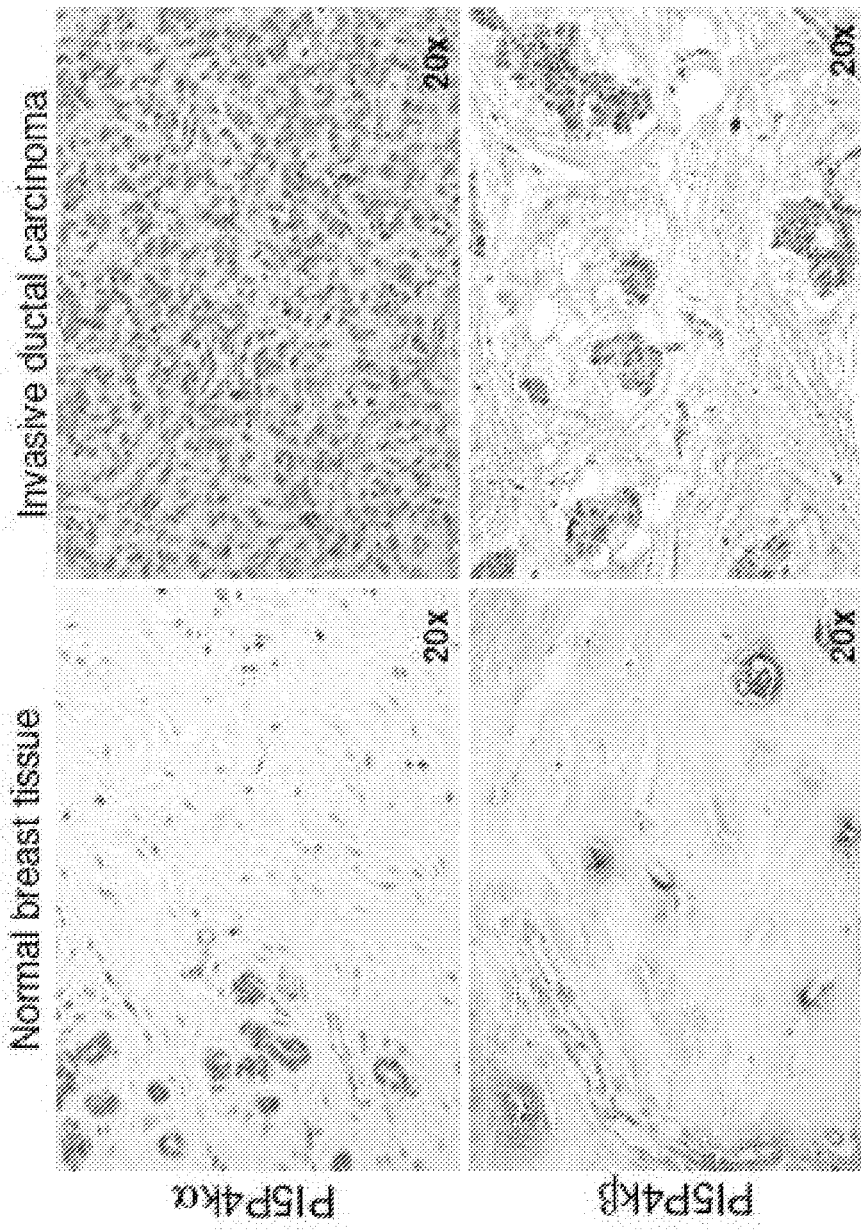
FIG. 2B shows that PI5P4K expression is up-regulated in a subset of breast cancer patients: immunohistochemistry (IHC) images from breast tumor and normal samples show PI5P4Kα and PI5P4Kβ staining)

Expression of PI5P4K in cancer cells appears critical for tumor cell growth and proliferation in vivo (FIG. 2A). Additional experiments also show that PI5P4K expression is upregulated in a subset of breast cancer patients (FIG. 2B).

Figure 3A:
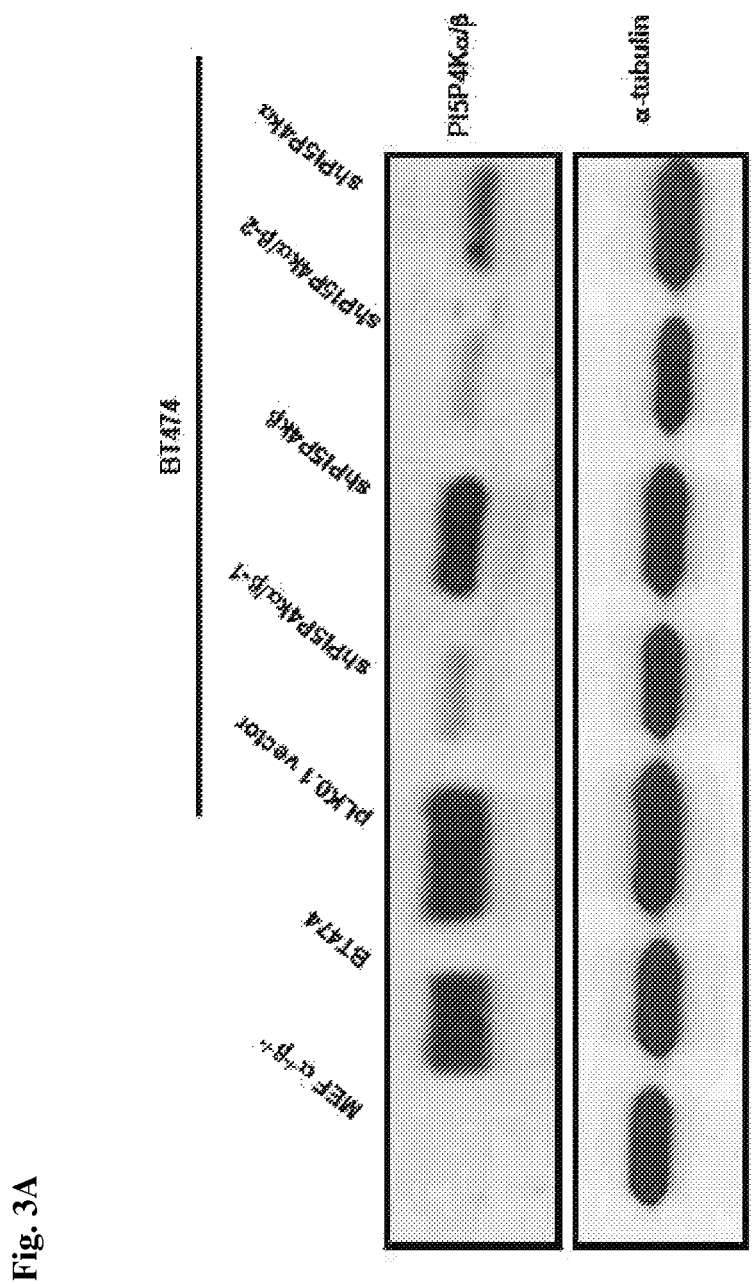
FIG. 3A shows the stable knockdown of PI5P4Kα/β in BT474 cells: in these experiments, an anti-α tublin antibody was used as the loading control.
Figure 3B:
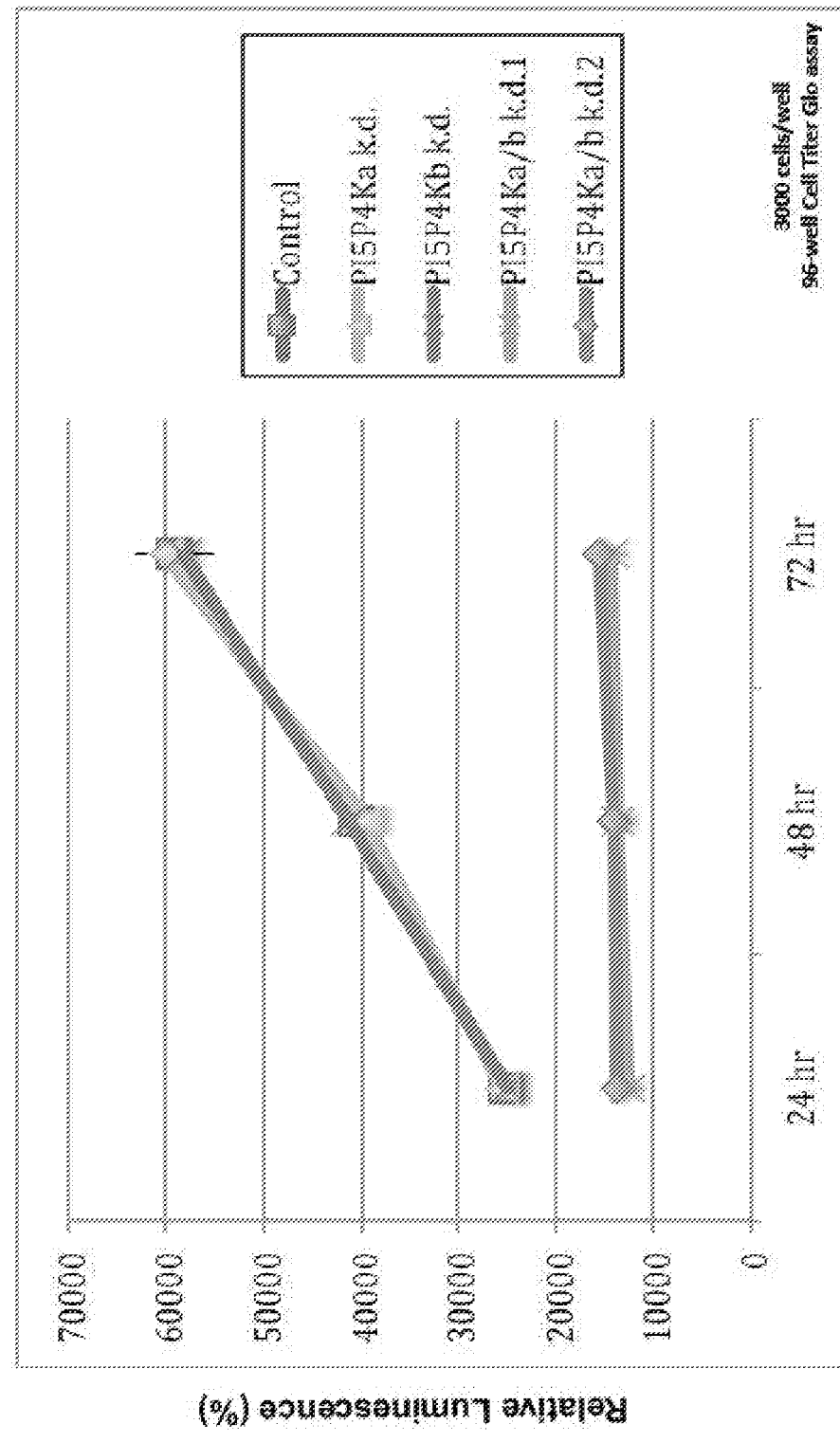
FIG. 3B shows the luminescent cell viability assay in stable PI5P4Kα/β knockdown cells. The data show that knockdown of PI5P4Kα/β inhibits proliferation.

Using shRNA constructs directed against the PI5P4Kα and β genes we have recently discovered that decreased PI5PK4 expression is accompanied by an increase in PI5P levels and an inhibition of cell proliferation in p53 null breast cancer cells (FIG. 3A and FIG. 3B).

Figure 4:
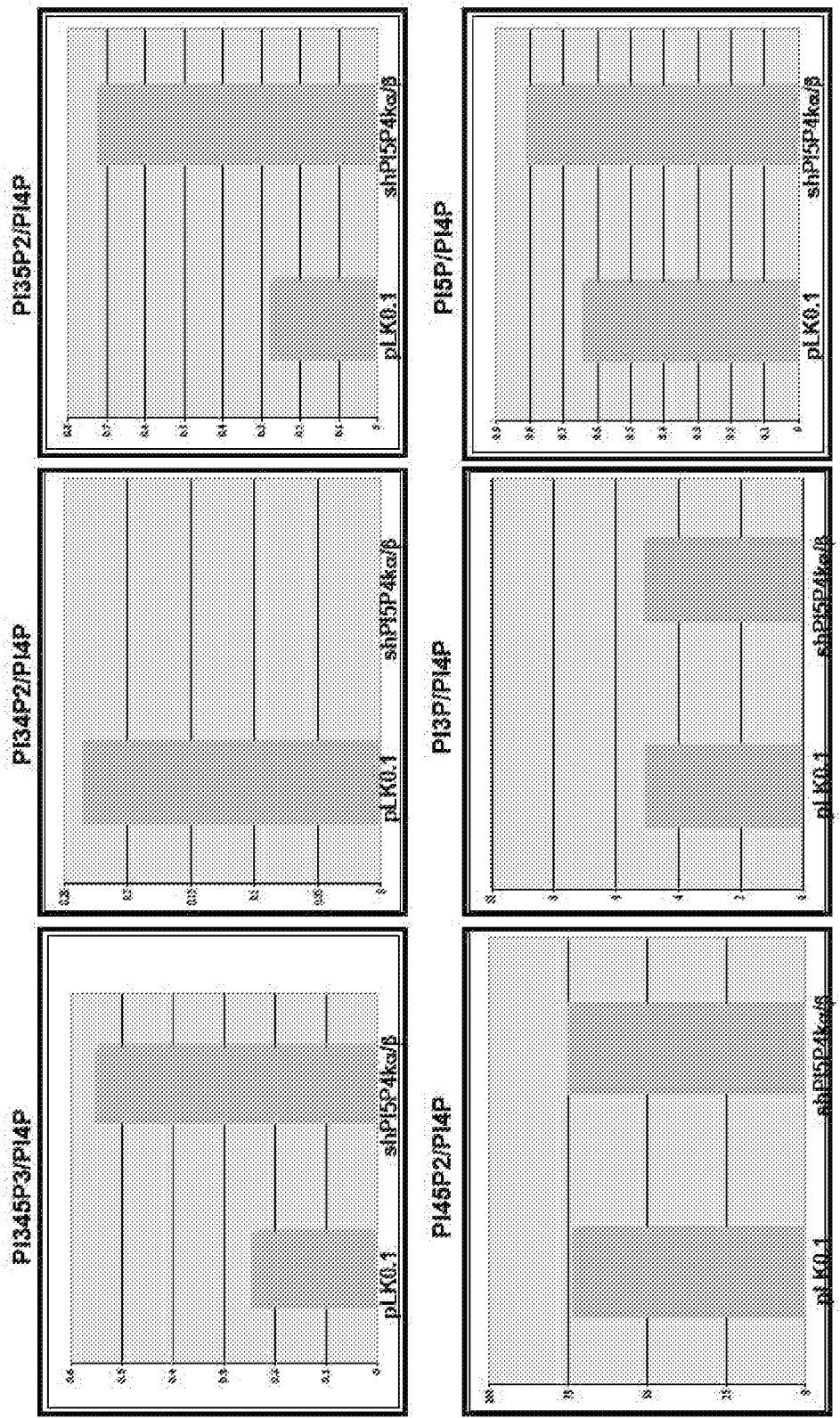
FIG. 4 shows phosphoinositide measurements in PI5P4Kα/β knockdown cells. BT474 PI5P4Kα/β knockdown cells (shPI5P4Kα/β) or control vector cells (pLK0.1) labeled with [3H]-inositol for 48 hours. Deacylated lipids were analyzed by HPLC, quantified and normalized to PI4P levels. Results are the average of two independent experiments.

FIG. 4 shows phosphoinositide measurements in PI5P4α/β knockdown cells. BT474 PI5P4Kα/β knockdown cells (shPI5P4Kα/β) or control vector cells (pLK0.1) labeled with [3H]-inositol for 48 hours. Deacylated lipids were analyzed by HPLC, quantified and normalized to PI4P levels. Results are the average of two independent experiments.

Figure 5A:
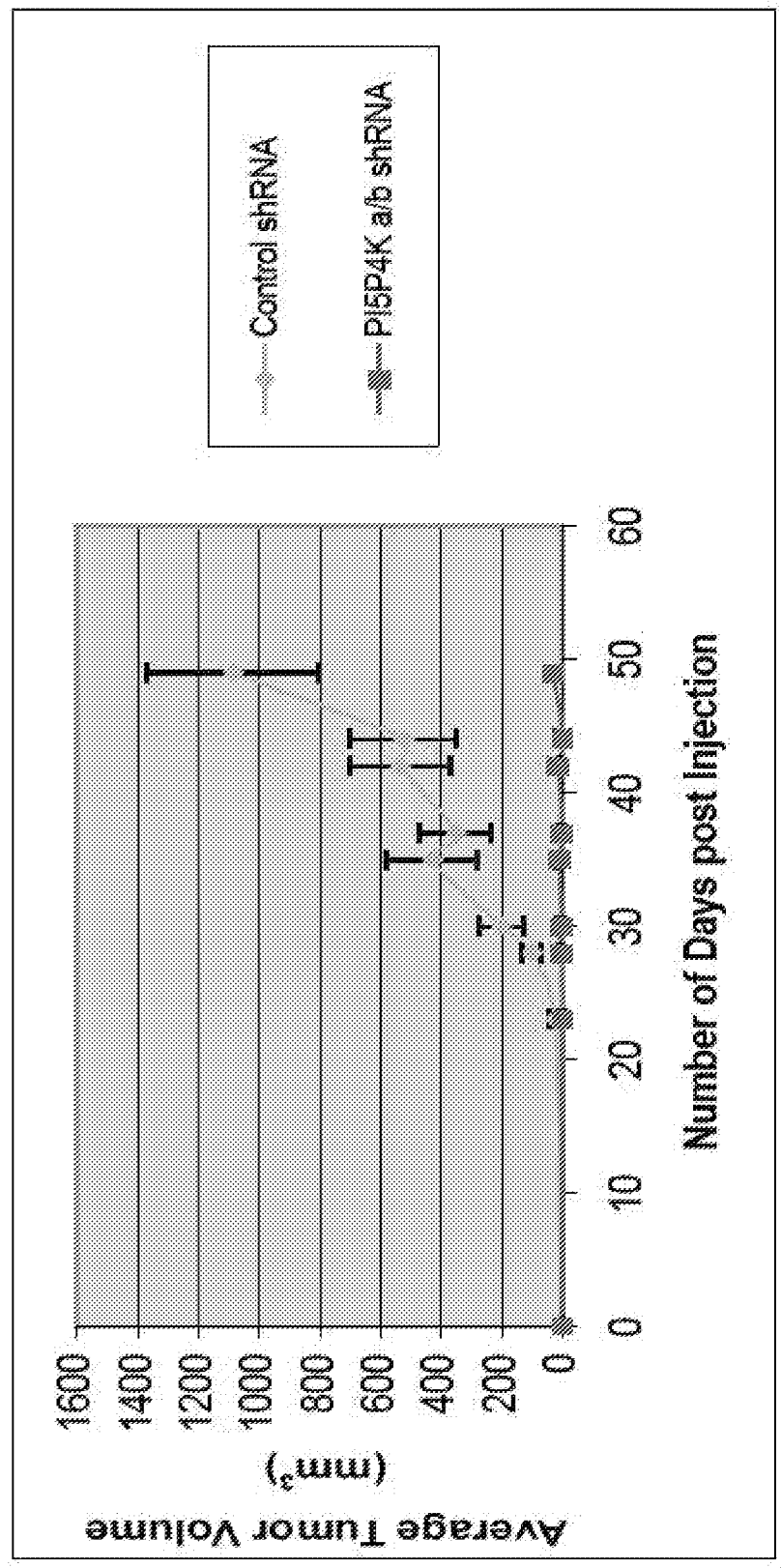
FIGS. 5A-5C show that PI5P4Kα/β knockdown cells fail to form tumors in a xenograft model.
Figures 5B, 5C:
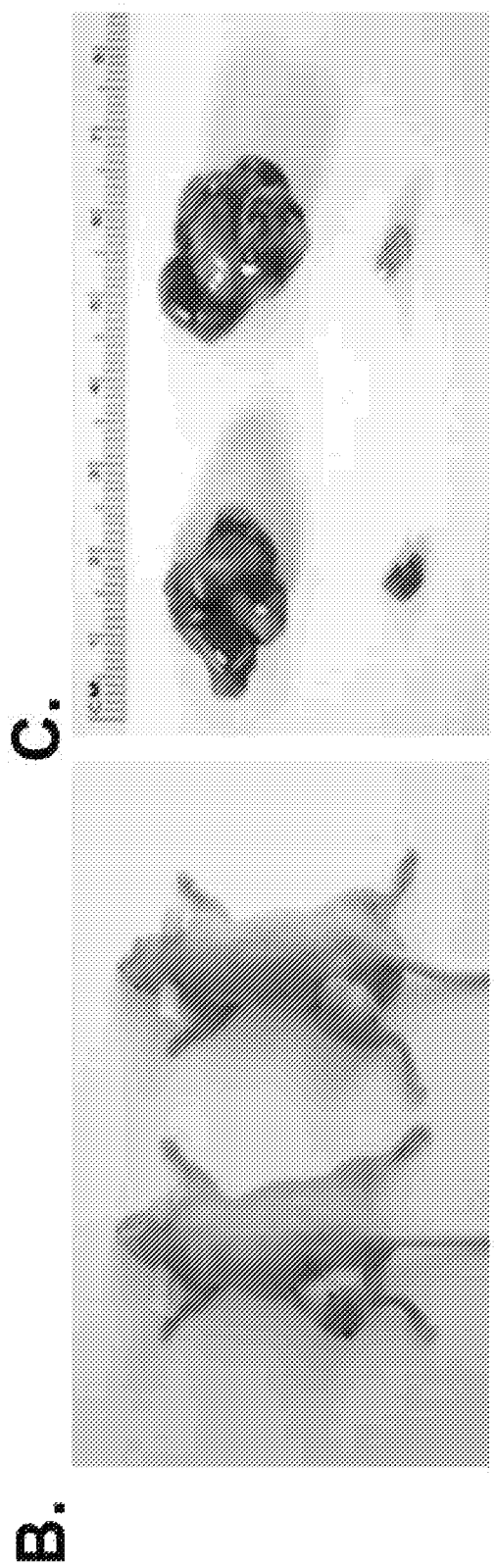
Figure 6:
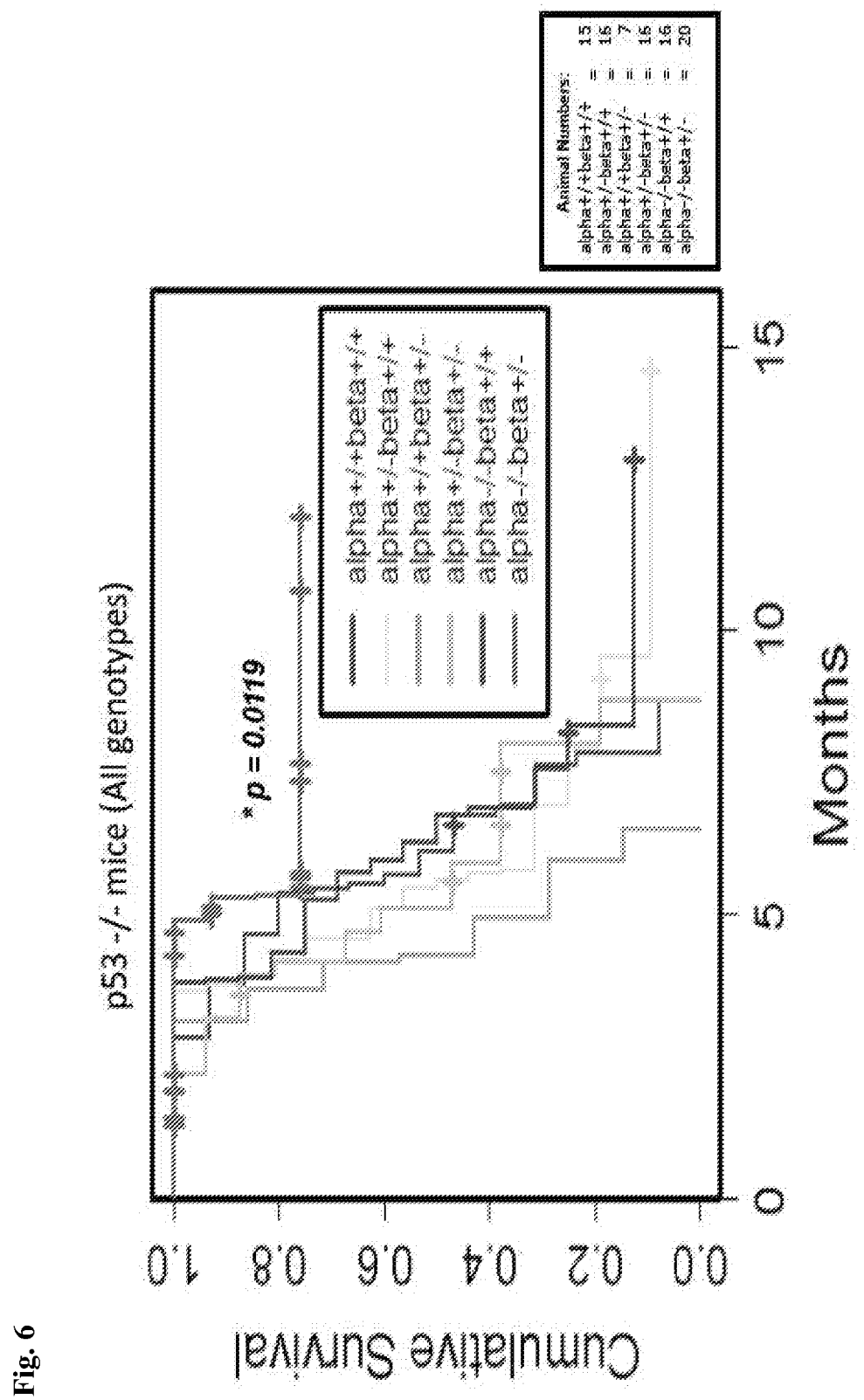
FIG. 6 shows PI5P4K deficiency restricts tumor death. Kaplan-Meier plot analysis of cumulative survival of indicated mouse genotypes.

In addition, the shRNA knockdown in p53 null breast cancer cells fail to form tumors in nude xenograft mouse models and the vector control knockdown cells form tumors (FIGS. 5A-5C). FIG. 5A shows tumor formation over time in nude mice injected with the BT474 cancer cell line expressing shRNA control or shRNA PI5P4K α/β. FIG. 5B shows tumor growth in mice (shPI5P4Kα/β (right flank) or pLK0.1 control cells (left flank)). FIG. 5C shows pictures of tumors after mice were euthanized. shPI5P4Kα/β (bottom) and pLK0.1 control cells (top). Further, PI5P4K deficiency restricts tumor death, as shown in a Kaplan-Meier plot analysis of cumulative survival of indicated mouse genotypes (FIG. 6).

The shRNA experiments demonstrate that loss of PI5P4K is accompanied by an increase in PI5P levels detrimental to p53 mutated cancer cell growth. Together, these data demonstrate a critical role for PI5P4K in tumor cell growth and support a potential role in oncogenesis for PI5P4K.

Example 2

Microarray analysis and metabolomics analysis have also been performed on PI5P4Kα/β knockdown cells. The BT474 breast cancer cell line was infected with lentivirus encoding either PI5P4Kα and β or the pLK0.1 vector control. Total RNA was extracted by using RNeasy mini kit (QIAGEN). The BIDMC Genomics and Proteomics Core generated probe was then hybridized to the Affymetrix Human Genome U133 Plus GeneChip Probe Array.

Figure 7A:
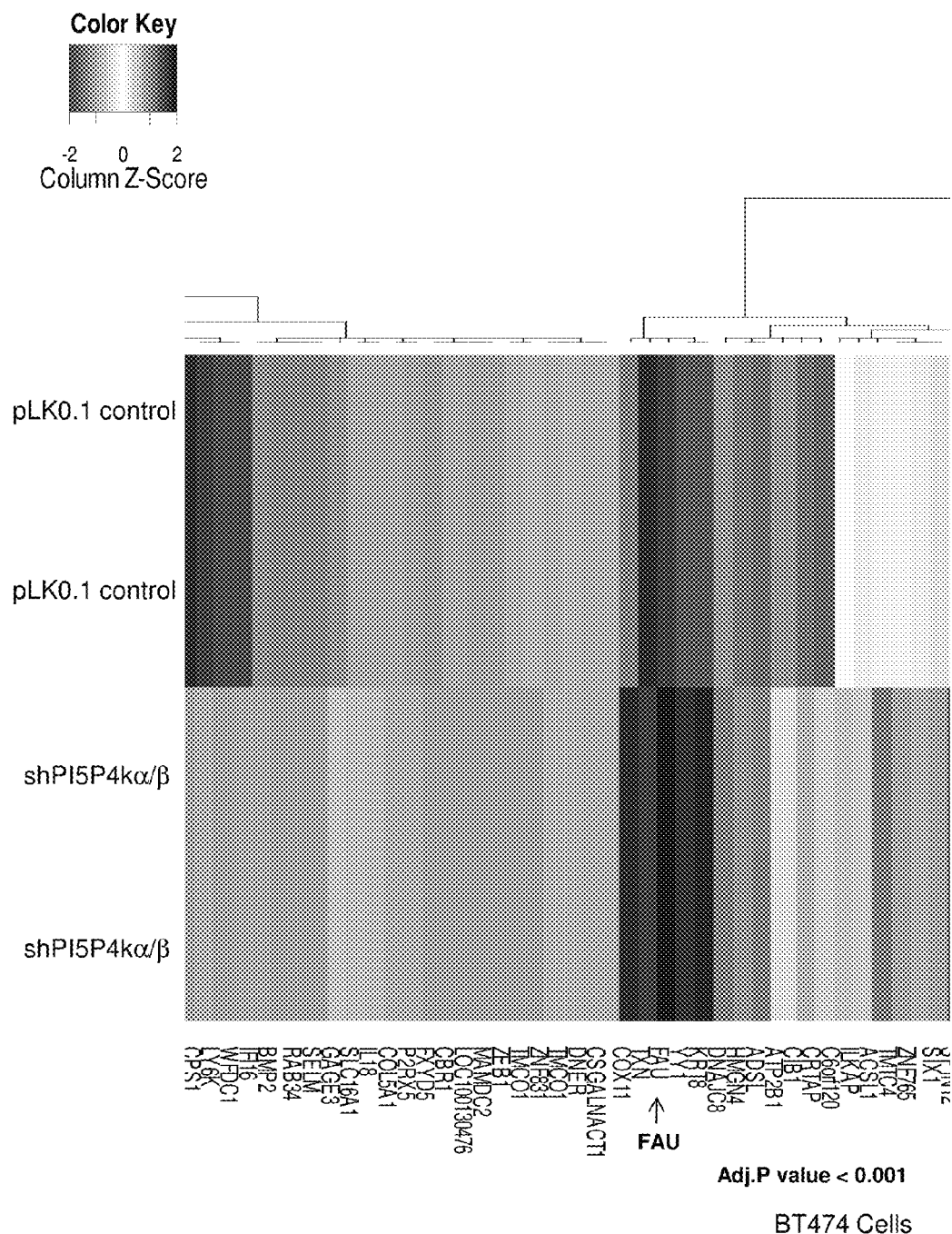
FIGS. 7A-7C show the microarray analysis show the microarray analysis of PI5P4Kα/β knockdown cells and provide expression data of BT474 PI5P4Kα/β knockdown cells (shPI5P4Kα/β) or control vector cells (pLK0.1) using Affymetrix Human Genome U133 Plus (~40,000 genes).
Figure 7A:
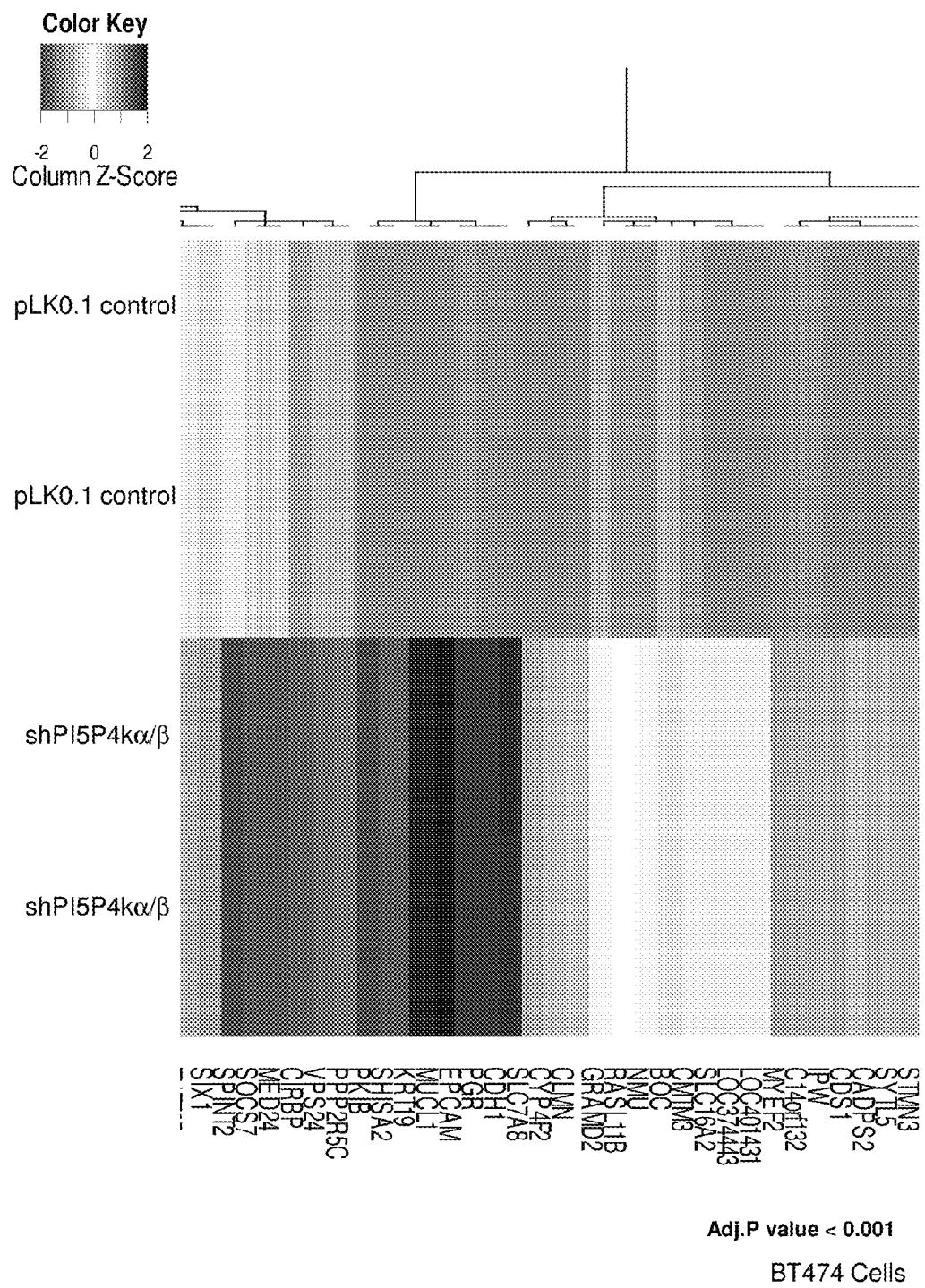
Figure 7A:
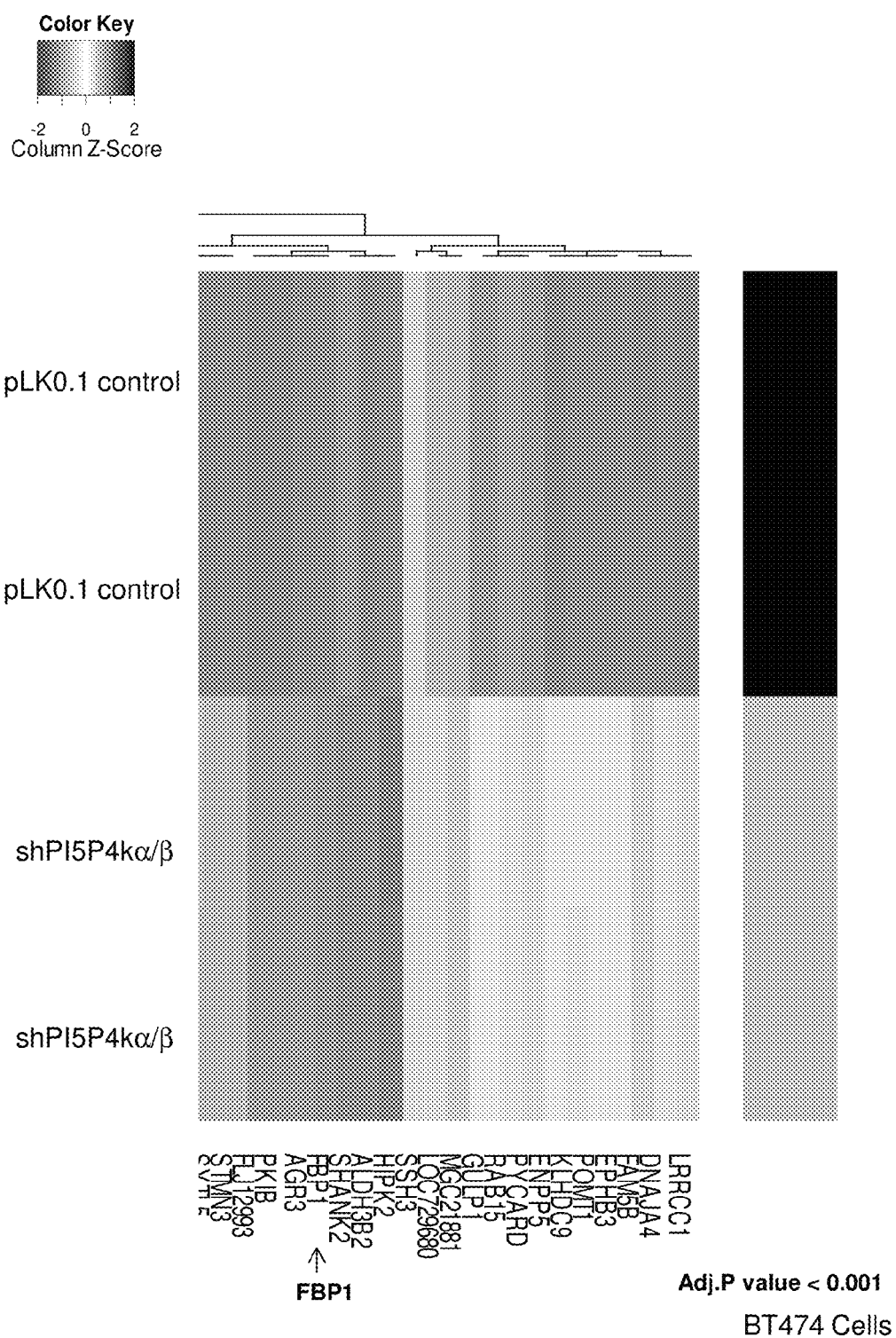
Figure 7A:
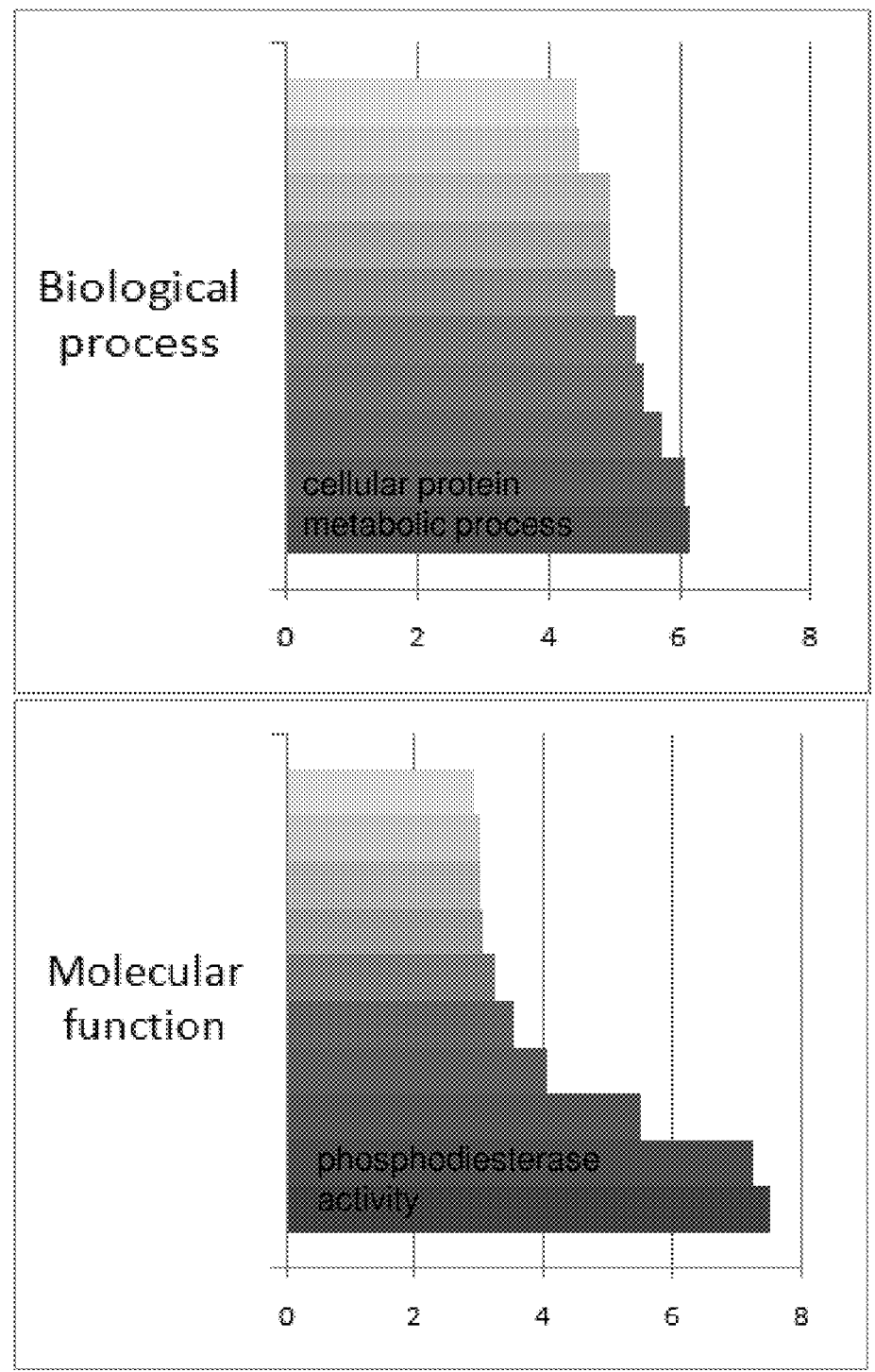
Figure 7A:
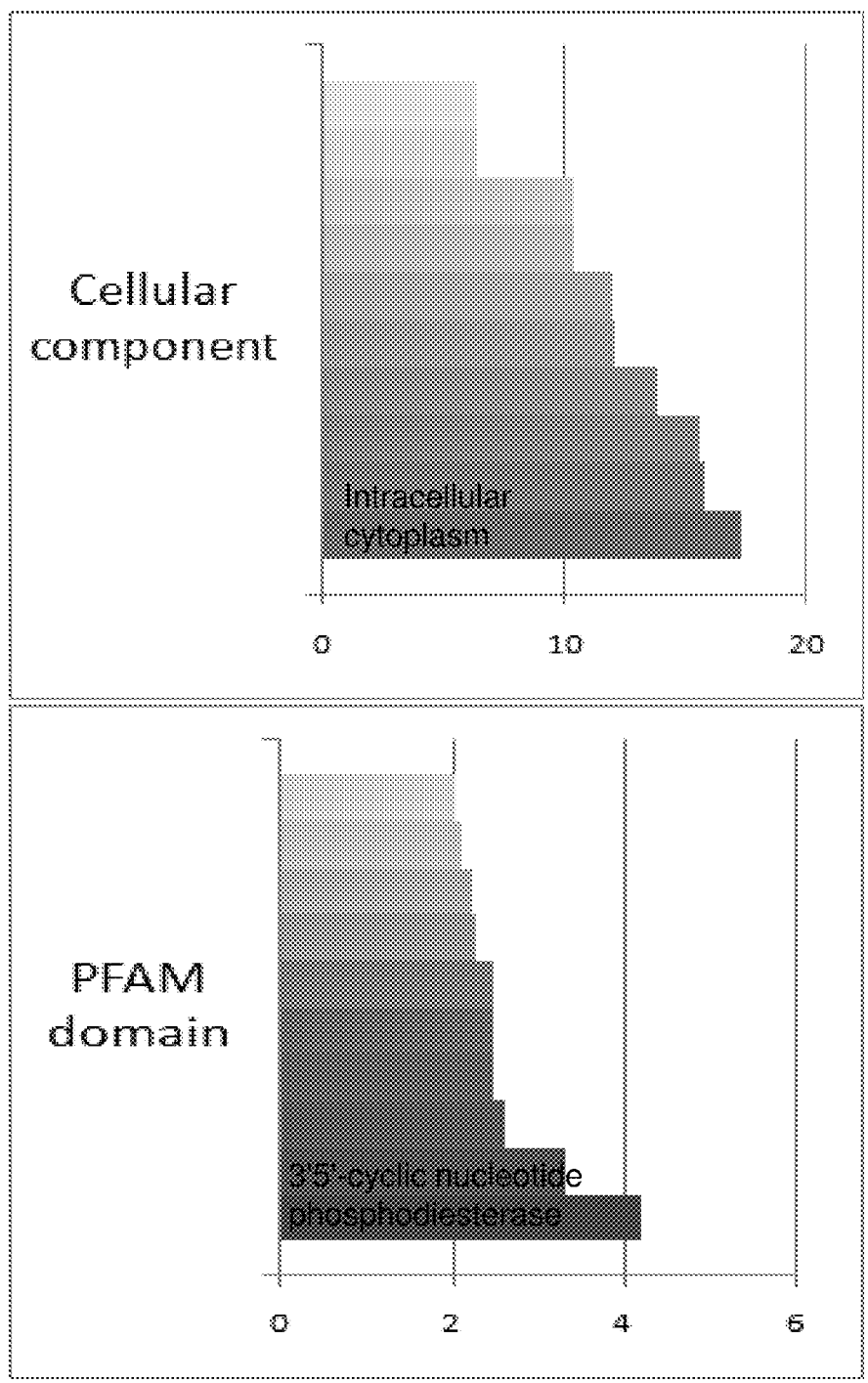
Figure 7B:
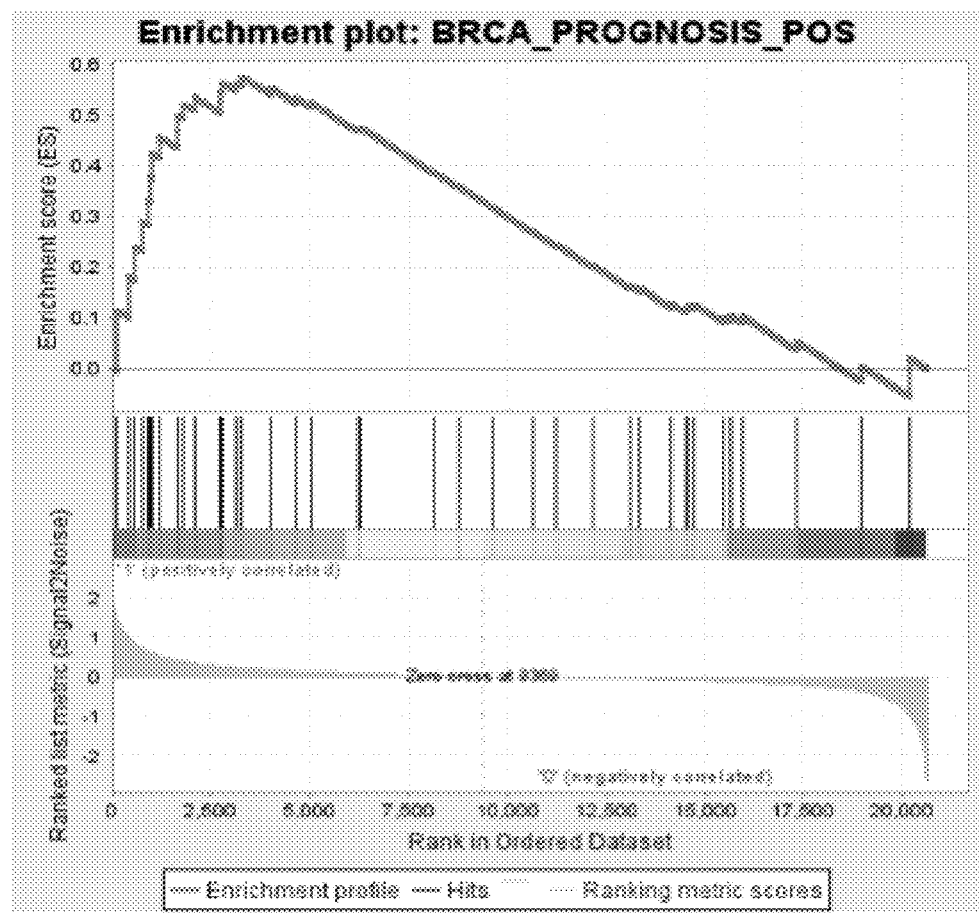
Figure 7B:
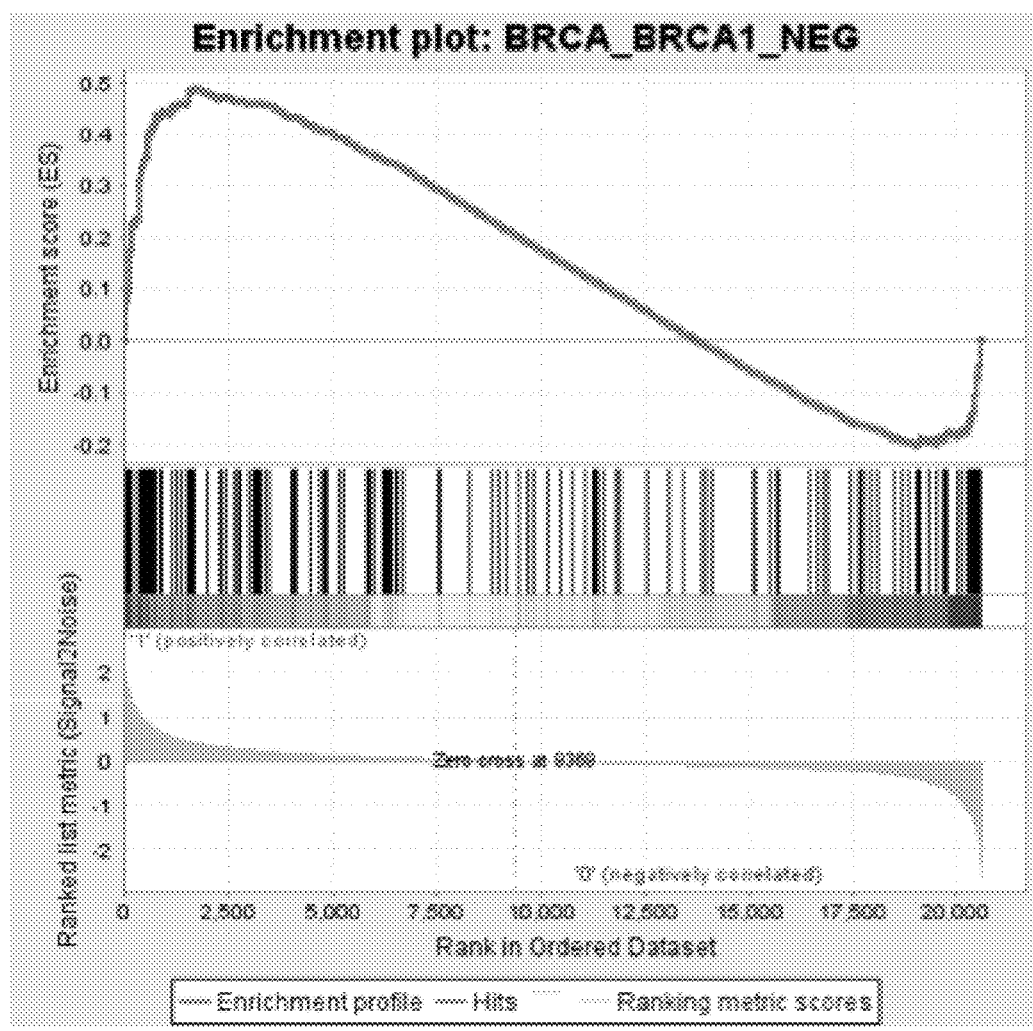
Figure 7B:
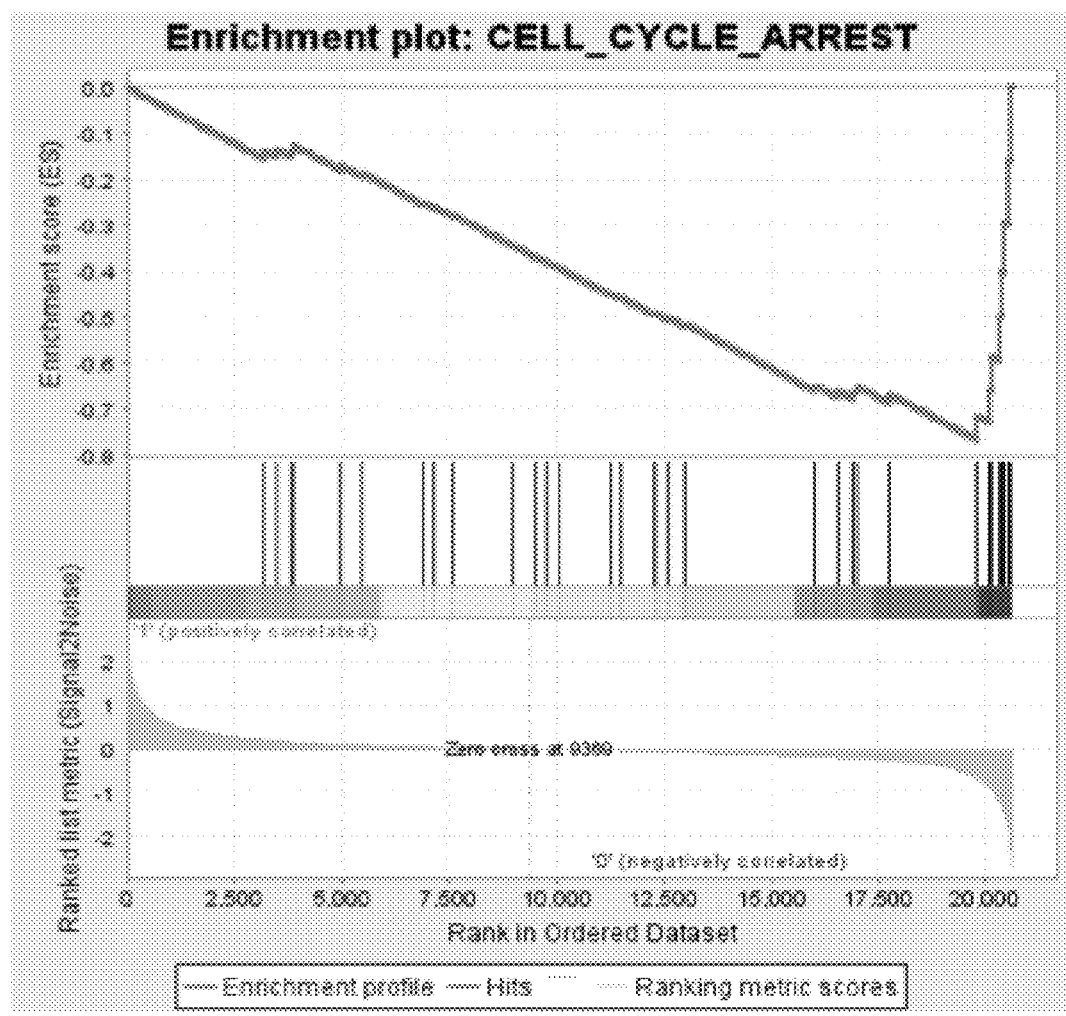
Figure 7C:
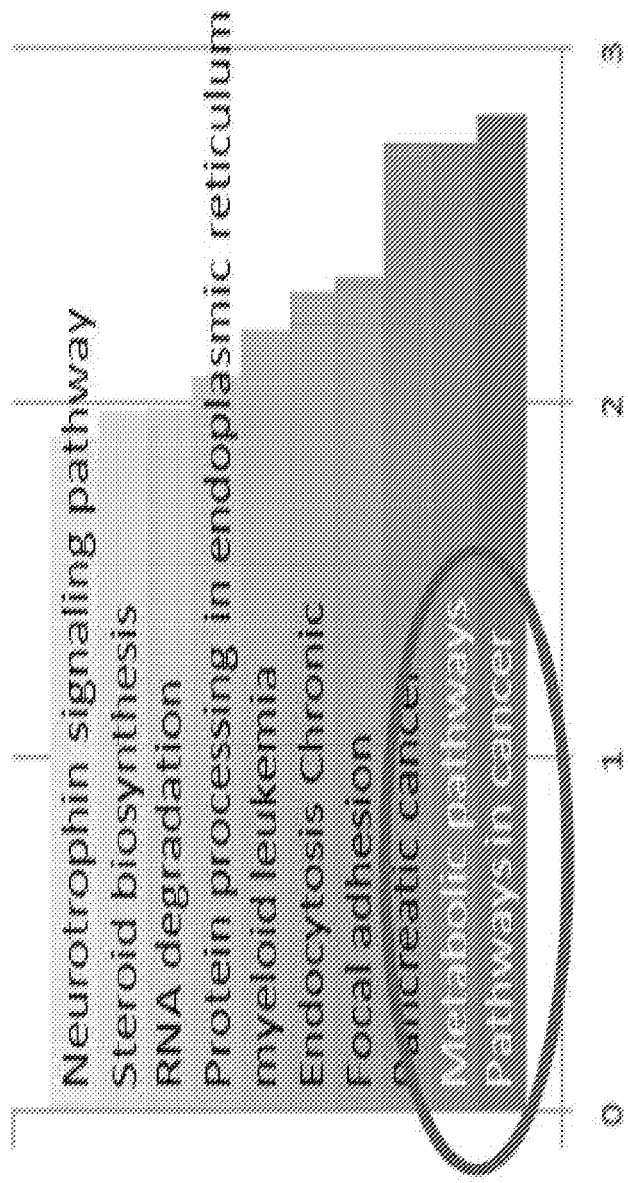

To further explore the PI5P4Kα/β double knockdown cells phenotype, microarray analysis of the BT474 pLK0.1 vector control cells was performed and then compared to the shPI5P4Kα/β double knockdown cells in triplicate using the Affymetrix Human Genome U133 Plus array (~40,000 genes). FIGS. 7A-7C show the microarray analysis of PI5P4Kα/β knockdown cells and provide expression data of BT474 PI5P4Kα/β knockdown cells (shPI5P4Kα/β) or control vector cells (pLK0.1) using Affymetrix Human Genome U133 Plus (~40,000 genes). FIG. 7A shows the heat map of differentially expressed genes with adjusted p value <0.001. FIGS. 7B and 7C show the Gene Set Enrichment Analysis (GSEA) and KEGG pathway analysis of gene set (shPI5P4Kα/β vs. pLK0.1 control).

Metabolomics analysis of BT474 PI5P4Kα/β knockdown cells (shPI5P4Kα/β) or control vector cells (pLK0.1) showed striking differences between 200 known metabolites, particularly differences in biological processes. The Gene Set Enrichment Analysis (GSEA) shows a positive correlation with breast cancer prognosis, a negative correlation with the BRAC1 signature, and a positive correlation with cell cycle arrest in the double knockdown cells versus the control cells. Further, KEGG pathway analysis indicates that the most significant pathway regulated by PI5P4K are metabolic pathways and pathways in cancer.

Example 3

Figure 8:
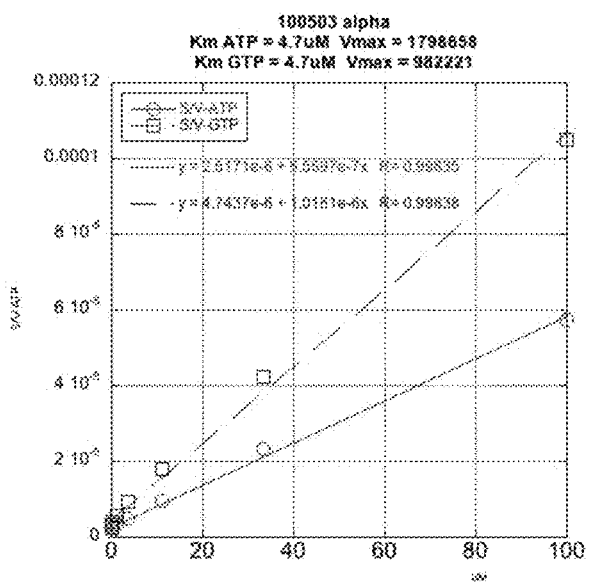
FIG. 8 shows that PI5P4Kα utilizes ATP and GTP. A Hanes-Woolf plot shows that PI5P4K' Km for ATP and GTP are comparable.
Figure 9:
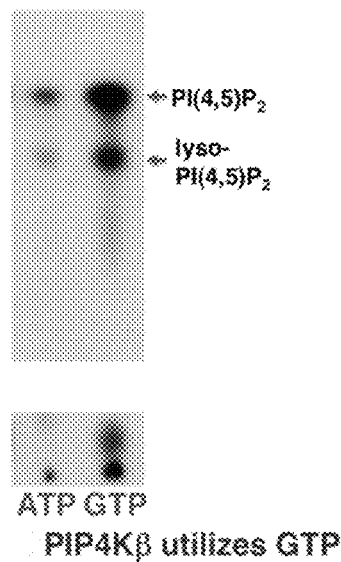
FIG. 9 shows that PI5P4Kβ utilizes GTP more than ATP.
Figure 10:
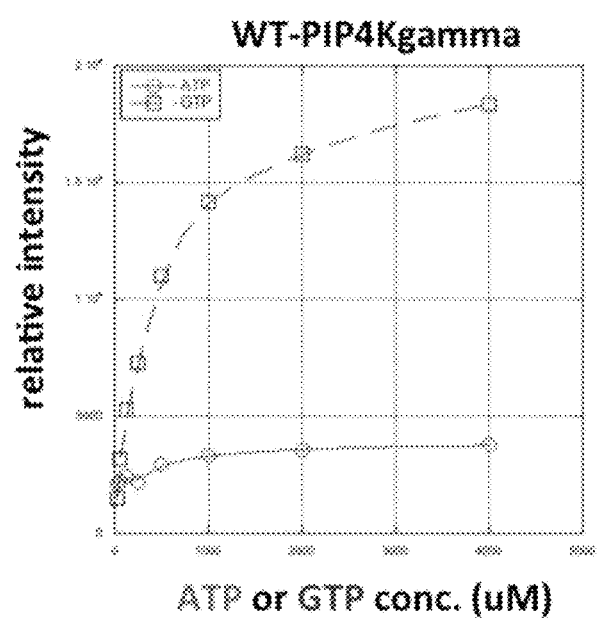
FIG. 10 shows that PI5P4Kγ utilized GTP exclusively.

We have also discovered that the PI5P4Kα isoform equally utilizes both ATP and GTP (FIG. 8), while the PI5P4Kβ isoform favors GTP over ATP (FIG. 9). Furthermore, the PI5P4Kγ isoform, which has been shown to be a dead kinase, actually has activity with GTP (FIG. 10).

Example 4

The findings of Example 3 can be used to screen for inhibitors or activators of PI5P4K using GTP as the substrate. Accordingly, modulators of PI5P4K can be identified using, for example, the series of procedures described below.

Step 1. Identification of Lead Compounds Using Quantitative High Throughput Screening A luminescent 1,536-well assay has been developed and validated for PI5P4K that measures ATP consumption by firefly luciferase. This assay can be used to screen the MLSMR as a concentration-titration series using the National Institutes of Health Chemical Genomics Center (NCGC) unique quantitative high-throughput screening (qHTS) platform. In this method, concentration-response curves (CRCs) are generated at the level of the primary screen. In qHTS, lead compounds are defined based on the quality and nature of the CRCs and structure-activity relationships (SAR) can be derived by clustering compounds associated with the highest quality CRCs by chemical similarity.

Step 2. Characterization and Optimization of Lead Compounds

Lead compounds identified according the procedure described in Step 1 can be validated using a firefly luciferase assay or, alternatively, by reading ADP production. These assays are available in 1536-well format at the NCGC. The selected compounds can also be evaluated in secondary assays for activity against the human Type I PI4P5K and Type III PI3P5K (Fab1/PIKfyve) in the firefly luciferase assay to determine selectivity for Type II PI5P4K.

Firefly Luciferase Assay

This assay uses the same buffer as the PI5P 4-kinase assay except no PI5P 4-kinase is added to the assay. This luciferase counterscreen has been performed at the NCGC against a large portion of the MLSMR (PubChem AID: 411) and has been used to define the chemotypes that interfere with firefly luciferase assays (Auld et al., *J. Med. Chem.* 51:2372, 2008).

ADP Generation

An orthogonal assay that is available is to measure ADP generation, instead of monitoring consumed ATP amount by luciferase. This provides for an alternative detection of PI5P4K activity and can be used to determine kinetic parameters and mechanism of action for inhibitors.

Cell-Based Assays

Lead compounds can also be studied in cell-based assays to examine the effect of these chemical probes on AKT-activation and cell proliferation. Cell based assays may be repeated using cells lacking PI5P4Kα and β to validate that effects observed in cells are due to PI5P4K activity modulation. These results can be used to further improve the potency of the lead compounds using structure-based methods, analogue synthesis, and medicinal chemical principles known in the art.

Step 3—In Vivo Analysis of the Lead Compounds on Cancer Cell Metabolism and Cell Proliferation.

Mouse tumor models are known available including models of breast and prostate cancer. PI5P4K inhibitors can be used in these animal models for efficacy in showing tumor suppressive properties. Further, the lead compounds identified according to the methods described herein can be used to investigate how PI5P4K regulation controls cellular metabolism.

Testing Activity in Cells: Effect on Cellular PI5P Level

Immortalized mouse embryonic fibroblasts (MEFs) can be prepared from PI5P4kα$^{-/-}$β$^{-/-}$ mice and wild-type mice. As a first step, lead compounds will be incubated with cells, and cellular PI5P levels can be measured using a standard HPLC method as known in the art (Rameh et al., *Nature*, 390:192, 1997). These experiments can identify cell membrane permeable compounds, as well as determine specificity of the compounds in cellular conditions. Validated PI5P4K inhibitors should increase cellular PI5P in the wild-type MEFs, but not in the PI5P4kα$^{-/-}$β$^{-/-}$ MEFs.

Given that PI5P4K regulates AKT activity though modulating cellular PI5P levels, inhibitors of PI5P4K can be expected to alter AKT activity in cells. Accordingly, monitoring AKT activity can be a useful and sensitive method to further study the compounds. AKT activity can be measured using phospho-T308-AKT and phosho-S473-AKT antibodies. To test if the AKT activity changes are due to an on-target effects of the compounds, these experiments can be repeated in cells lines with shRNA knockdown of endogenous PI5P4Kα/β.

Testing Activity in Cells: Effect on Cell Survival and Proliferation

The lead compounds can also be studied to determine whether they can induce cell death or alter cell proliferation. At time points following compound addition, cell death can be assessed using propidium iodide exclusion as measured by flow cytometry (Vander Heiden et al., *Mol. Cell. Biol.* 21:5899, 2001). Cell proliferation assays can be performed in parallel by counting cells at defined intervals in the presence of active compound. These experiments can be executed under standard tissue culture conditions. Cell lines that have p53 mutations and in which cell proliferation is halted upon PI5P4K knockdown can be used in these experiments. Additionally, cell line that have intact p53 and are insensitive to PI5P4K knockdown can also be used for comparative purposes.

Other Embodiments

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth.

All references, patents, patent application publications, and patent applications cited herein are hereby incorporated by reference to the same extent as if each of these references, patents, patent application publications, and patent applications were separately incorporated by reference herein.

What is claimed is:

1. A method for identifying a compound that inhibits phosphatidylinositol-5-phosphate-4-kinase (PI5P4K), said method comprising:
   (a) providing a cell expressing a phosphatidylinositol-5-phosphate-4-kinase (PI5P4K) and comprising a p53-inactive mutation or a p53-deletion and a substrate;
   (b) contacting said cell with a candidate compound;
   (c) detecting the activity of said PI5P4K; and
   (d) determining if said candidate compound inhibits said PI5P4K;
   wherein said candidate compound is a preferred candidate for treating a p53-mutated cancer if said candidate compound inhibits said PI5P4K, and wherein said cell is not a leukemia cell.

2. The method of claim 1, wherein said substrate is guanosine-5'-triphosphate (GTP).

3. The method of claim 1, wherein said PI5P4K is the PI5P4Kβ isoform.

4. The method of claim 1, wherein said substrate is adenosine-5'-triphosphate (ATP).

5. The method of claim 1, wherein said PI5P4K is the PI5P4Kα isoform.

6. The method of claim 1, wherein said method further comprises comparing the activity detected in step (c) with the detected activity of PI5P4K in a medium not contacted with said candidate compound of step (b), wherein decreased activity of PI5P4K in the presence of said candidate compound of step (b) identifies said candidate compound as said preferred candidate.

7. The method of claim 1, wherein said method further comprises comparing the activity detected in step (c) with the activity observed in a medium where said PI5P4K is absent.

8. The method of claim 1, wherein said PI5P4K is human recombinant PI5P4K.

9. The method of claim 1, wherein said cell is a mouse embryonic fibroblast (MEF).

10. The method of claim 9, wherein said MEF is an immortalized MEF.

11. The method of claim 10, wherein said activity detected in step (c) is compared with the activity observed in a medium where said PI5P4K is absent.

12. The method of claim 11, wherein said activity detected in step (c) is the production of cellular phosphatidylinositol-5-phosphate (PI5P).

13. The method of claim 11, wherein said medium where said PI5P4K is absent comprises an immortalized MEF prepared from PI5P4Kα$^{-/-}$β$^{-/-}$ knockout mice.

14. The method of claim 12, wherein the levels of said cellular phosphatidylinositol-5-phosphate (PI5P) increase compared to the levels of PI5P in MEFs prepared from PI5P4Kα$^{-/-}$β$^{-/-}$ knockout mice.

15. The method of claim 1, wherein said activity detected in step (c) is AKT activity.

16. The method of claim 15, wherein said AKT activity is detected using an AKT specific antibody.

17. The method of claim 16, wherein said AKT specific antibody is the phospho-T308-AKT or phospho-S473-AKT antibody.

18. The method of claim 1, wherein, said activity detected is step (c) is the consumption of GTP.

19. The method of claim 1, wherein said PI5P4K activity is detected using absorbance, fluorescence, Raman scattering, phosphorescence, luminescence, luciferase activity, or radioactivity; and said PI5P4K activity is optionally quantified using absorbance, fluorescence, Raman scattering, phosphorescence, luminescence, luciferase activity, or radioactivity.

20. The method of claim 1, wherein said cell has a p53 inactive mutation.

21. The method of claim 20, wherein said cell is a p53-mutated cancer cell.

22. The method of claim 1, wherein said cell is a p53-null cell.

23. The method of claim 1, wherein said cell is a breast cancer cell.

24. The method of claim 1, wherein said activity detected in step (c) is detected by a cell proliferation assay.

* * * * *

SEQUENCE LISTING

```
<160> NUMBER OF SEQ ID NOS: 16

<210> SEQ ID NO 1
<211> LENGTH: 21
<212> TYPE: DNA
<213> ORGANISM: Homo sapiens

<400> SEQUENCE: 1
cctcggacag acatgaacat t                                            21

<210> SEQ ID NO 2
<211> LENGTH: 57
<212> TYPE: DNA
<213> ORGANISM: Homo sapiens

<400> SEQUENCE: 2
ccggcctcgg acagacatga acattctcga gaatgttcat gtctgtccga ggttttt    57

<210> SEQ ID NO 3
<211> LENGTH: 58
<212> TYPE: DNA
<213> ORGANISM: Artificial Sequence
<220> FEATURE:
<223> OTHER INFORMATION: Synthetic Construct

<400> SEQUENCE: 3
ccggcctcgg acagacatga acattctcga gaatgttcat gtctgtccga ggtttttg   58
```

```
<210> SEQ ID NO 4
<211> LENGTH: 58
<212> TYPE: DNA
<213> ORGANISM: Artificial Sequence
<220> FEATURE:
<223> OTHER INFORMATION: Synthetic Construct

<400> SEQUENCE: 4
aattcaaaaa cctcggacag acatgaacat tctcgagaat gttcatgtct gtccgagg          58

<210> SEQ ID NO 5
<211> LENGTH: 21
<212> TYPE: DNA
<213> ORGANISM: Homo sapiens

<400> SEQUENCE: 5
cggcttaatg ttgatggagt t                                                  21

<210> SEQ ID NO 6
<211> LENGTH: 57
<212> TYPE: DNA
<213> ORGANISM: Homo sapiens

<400> SEQUENCE: 6
ccggcggctt aatgttgatg gagttctcga gaactccatc aacattaagc cgttttt           57

<210> SEQ ID NO 7
<211> LENGTH: 58
<212> TYPE: DNA
<213> ORGANISM: Artificial Sequence
<220> FEATURE:
<223> OTHER INFORMATION: Synthetic Construct

<400> SEQUENCE: 7
ccggcggctt aatgttgatg gagttctcga gaactccatc aacattaagc cgtttttg          58

<210> SEQ ID NO 8
<211> LENGTH: 58
<212> TYPE: DNA
<213> ORGANISM: Artificial Sequence
<220> FEATURE:
<223> OTHER INFORMATION: Synthetic Construct

<400> SEQUENCE: 8
aattcaaaaa cggcttaatg ttgatggagt tctcgagaac tccatcaaca ttaagccg          58

<210> SEQ ID NO 9
<211> LENGTH: 21
<212> TYPE: DNA
<213> ORGANISM: Homo sapiens

<400> SEQUENCE: 9
ccctcgatct atttccttct t                                                  21

<210> SEQ ID NO 10
<211> LENGTH: 57
<212> TYPE: DNA
<213> ORGANISM: Homo sapiens

<400> SEQUENCE: 10
ccggccctcg atctatttcc ttcttctcga gaagaaggaa atagatcgag ggttttt           57

<210> SEQ ID NO 11
<211> LENGTH: 58
```

```
<212> TYPE: DNA
<213> ORGANISM: Artificial Sequence
<220> FEATURE:
<223> OTHER INFORMATION: Synthetic Construct

<400> SEQUENCE: 11
ccggccctcg atctatttcc ttcttctcga gaagaaggaa atagatcgag ggtttttg        58

<210> SEQ ID NO 12
<211> LENGTH: 58
<212> TYPE: DNA
<213> ORGANISM: Artificial Sequence
<220> FEATURE:
<223> OTHER INFORMATION: Synthetic Construct

<400> SEQUENCE: 12
aattcaaaaa ccctcgatct atttccttct tctcgagaag aaggaaatag atcgaggg        58

<210> SEQ ID NO 13
<211> LENGTH: 21
<212> TYPE: DNA
<213> ORGANISM: Homo sapiens

<400> SEQUENCE: 13
caaacgcttc aacgagttta t                                                21

<210> SEQ ID NO 14
<211> LENGTH: 57
<212> TYPE: DNA
<213> ORGANISM: Homo sapiens

<400> SEQUENCE: 14
ccggcaaacg cttcaacgag tttatctcga gataaactcg ttgaagcgtt tgttttt         57

<210> SEQ ID NO 15
<211> LENGTH: 58
<212> TYPE: DNA
<213> ORGANISM: Artificial Sequence
<220> FEATURE:
<223> OTHER INFORMATION: Synthetic Construct

<400> SEQUENCE: 15
ccggcaaacg cttcaacgag tttatctcga gataaactcg ttgaagcgtt tgttttg         58

<210> SEQ ID NO 16
<211> LENGTH: 58
<212> TYPE: DNA
<213> ORGANISM: Artificial Sequence
<220> FEATURE:
<223> OTHER INFORMATION: Synthetic Construct

<400> SEQUENCE: 16
aattcaaaaa caaacgcttc aacgagttta tctcgagata aactcgttga agcgtttg        58
```